(12) United States Patent
Shiki

(10) Patent No.: US 7,874,988 B2
(45) Date of Patent: Jan. 25, 2011

(54) ULTRASONIC DIAGNOSTIC APPARATUS AND ULTRASONIC TRANSMISSION METHOD

(75) Inventor: Eiichi Shiki, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 567 days.

(21) Appl. No.: 11/499,732

(22) Filed: Aug. 7, 2006

(65) Prior Publication Data

US 2007/0038091 A1 Feb. 15, 2007

(30) Foreign Application Priority Data

Aug. 9, 2005 (JP) ............................. 2005-230300

(51) Int. Cl.
 *A61B 8/00* (2006.01)
(52) U.S. Cl. ...................... 600/443; 600/459; 600/447; 600/437
(58) Field of Classification Search ................. 600/437, 600/443, 447, 459
See application file for complete search history.

(56) References Cited

U.S. PATENT DOCUMENTS 4,815,043 A 3/1989 Shirasaka
5,235,982 A * 8/1993 O'Donnell .................. 600/443
5,856,955 A 1/1999 Cole et al.

FOREIGN PATENT DOCUMENTS

JP 7-71556 8/1995

* cited by examiner

*Primary Examiner*—Long V Le
*Assistant Examiner*—Nigel Fontenot
(74) *Attorney, Agent, or Firm*—Oblon, Spivak, McClelland, Maier & Neustadt, L.L.P.

(57) ABSTRACT

A reference condition generation unit of an ultrasonic diagnostic apparatus generates a reference delay condition and a reference amplitude condition for determining delay time and amplitude of a driving pulse to be supplied to a transducer element at the time of non-simultaneous and parallel reception. A transmission condition generation unit generates a transmission delay condition and a transmission amplitude condition for determining delay time and amplitude of a driving pulse to be supplied to a transducer element at the time of simultaneous and parallel reception, on the basis of the reference delay condition and the reference amplitude condition. A transmission unit sets the delay time and the driving amplitude of the driving pulse to be supplied to a plurality of adjacent transducer elements selected by an element selection unit among the transducer elements arranged in an ultrasonic probe, on the basis of the transmission delay condition and the transmission amplitude condition.

8 Claims, 15 Drawing Sheets

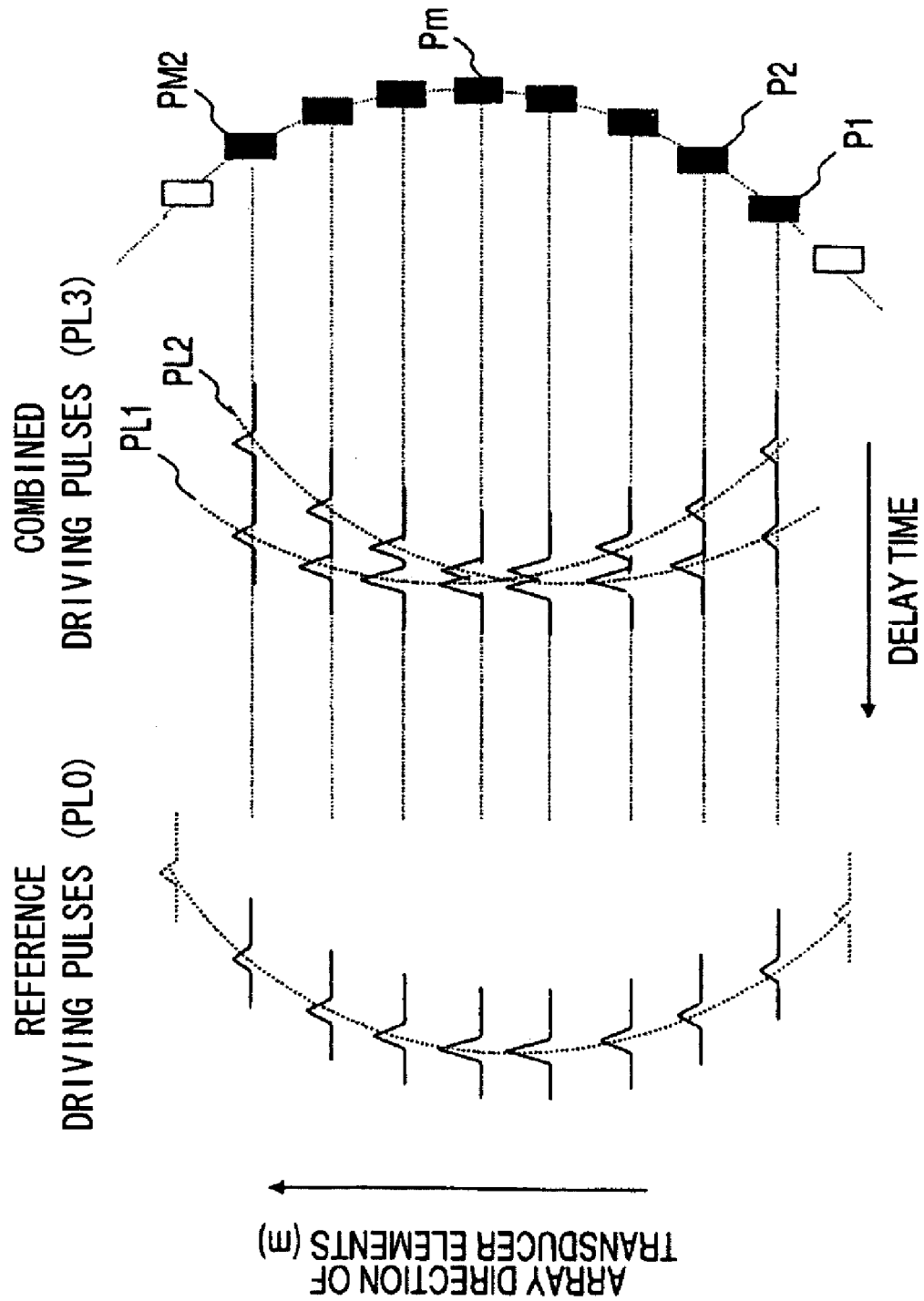

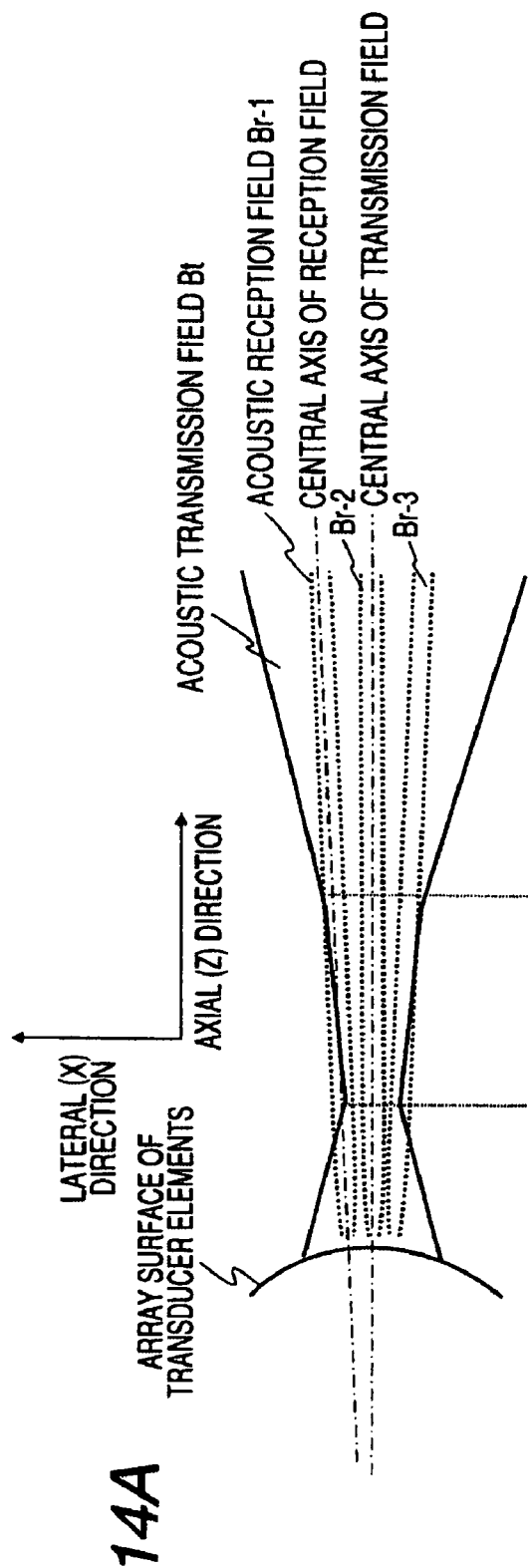
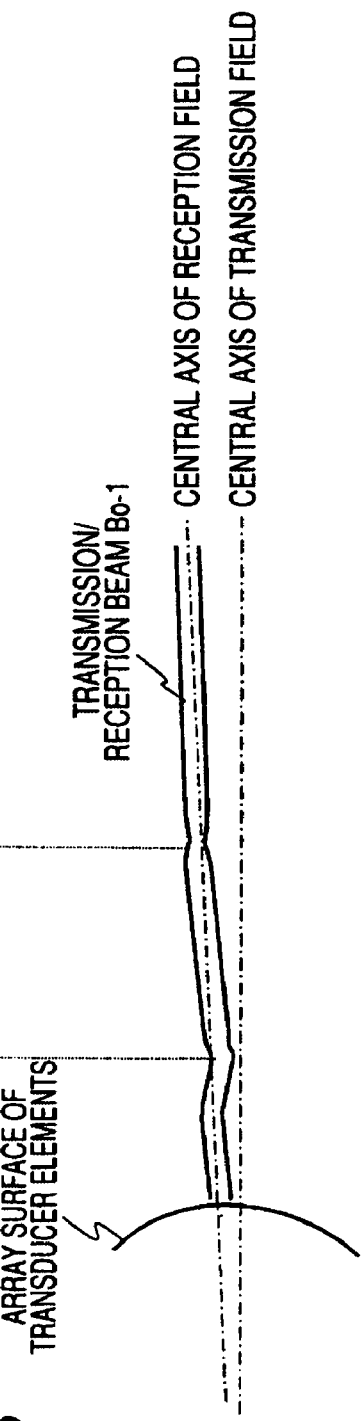
FIG. 14A
FIG. 14B

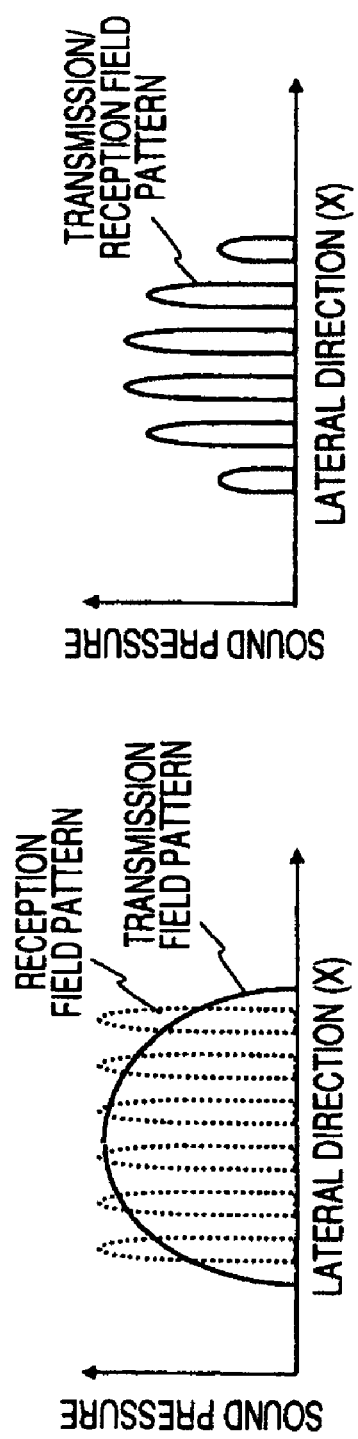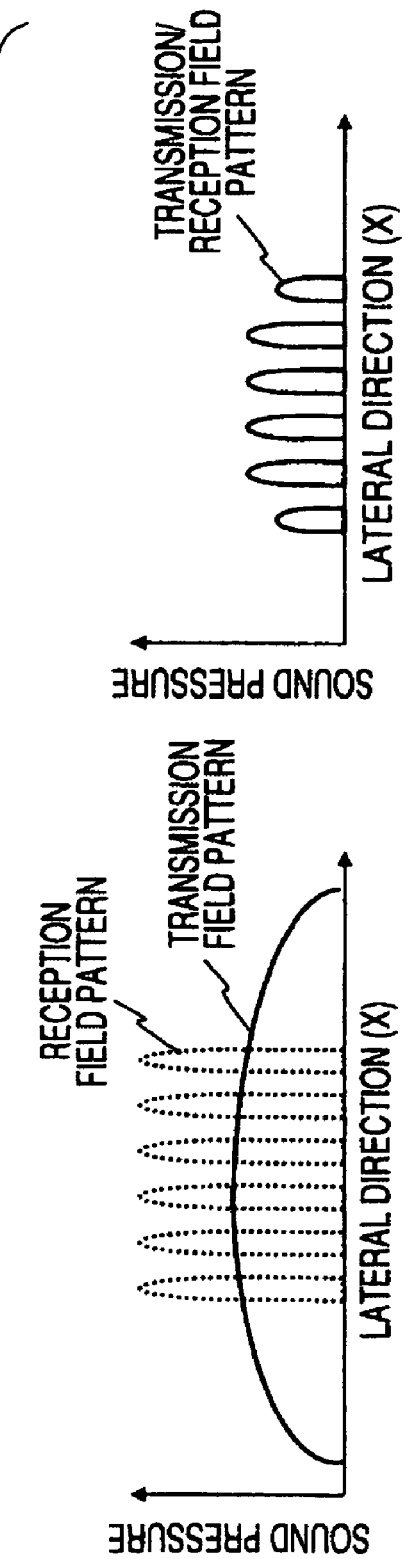

ULTRASONIC DIAGNOSTIC APPARATUS AND ULTRASONIC TRANSMISSION METHOD

CROSS-REFERENCE TO RELATED APPLICATIONS

This application is based upon and claims the benefit of priority from the prior Japanese Patent Application No.2005-230300 filed on Aug. 9, 2005, the entire contents of which are incorporated herein by reference.

FIELD OF THE INVENTION

The present invention relates to an ultrasonic diagnostic apparatus and an ultrasonic transmission method, and more particularly, to an ultrasonic diagnostic apparatus and an ultrasonic transmission method to perform receiving reflected ultrasound simultaneously from a plurality of directions simultaneously.

DESCRIPTION OF THE BACKGROUND

An ultrasonic diagnostic apparatus is designed to generate ultrasonic pulses from transducer elements disposed in an ultrasonic probe. The ultrasonic pulses are emitted into an object to be examined. The ultrasonic diagnostic apparatus receives reflected ultrasound produced due to differences in acoustic impedance among the tissues of the object. The ultrasonic diagnostic apparatus displays image data on a monitor, which is generated based on reception signals corresponding to the reflected ultrasound. This diagnostic method allows easy observation of real-time two-dimensional images by simple operation of only bringing the ultrasonic probe into contact with the body surface. The diagnostic method is widely used for functional diagnosis or morphological diagnosis of various organs in a living body.

An Ultrasonic diagnostic method, which obtains living body information by using reflected ultrasound from tissue or blood cells in the living body, have rapidly progressed along with two great technical developments of an ultrasonic reflection method and an ultrasonic Doppler method. And B-mode images and colored Doppler images obtained by these techniques have become indispensable to recent ultrasonic image diagnosis.

Nowadays, an electronic-scanning ultrasonic diagnostic apparatus most widely used has a plurality of transducer element arranged in one dimension and displays two-dimensional image data in real time by controlling the driving of the transducer elements at high speed.

In a color Doppler method for generating colored Doppler image data, moving objects such as blood corpuscles in predetermined cross section of a living body is scanned by the ultrasonic pulse and Doppler frequency shift of the reflected ultrasound corresponding to blood flow velocity is detected and imaged. The colored Doppler method was applied in the past to generate image data for intracardiac blood flow with high velocity, but has become applicable to generate image data for blood flow with low velocity such as blood flow in abdominal organs.

By the way, high measurement accuracy (low flow velocity detection capability and high flow velocity detection capability), temporal resolution, and spatial resolution are required for obtaining high diagnostic accuracy in the colored Doppler method. When ultrasonic pulses are emitted to moving objects and moving velocity of the objects is detected from the Doppler frequency shift of the reflected ultrasound, conventionally, the transmission and reception of the ultrasonic pulses with respect to the objects is repeatedly performed a plural number of times (L times) with a predetermined transmission interval Tr and the moving velocity is measured on the basis of a series of reflected ultrasound obtained in the observation time Tobs (Tobs=Tr·L).

In this case, the detection capability of low flow velocity (low flow velocity detection capability: lower limit of measurable flow velocity) Vmin is determined by a characteristic of a filter (for example, MTI filter) used to detect Doppler components from a series of reflected ultrasound obtained through the L-times ultrasonic transmission and reception, that is, a cut-off frequency and a shoulder characteristic of the filter. At this time, Vmin is expressed by Expression 1 when it is assumed that repetition frequency of the transmission (rate frequency) is fr (fr=1/Tr).

$$V\min \propto \frac{1}{Tobs} = \frac{fr}{L} \qquad (1)$$

On the other hand, the upper limit of measurable flow velocity (high flow velocity detection capability) Vmax is determined by nyquist frequency defined as a half of repetition frequency of the ultrasonic transmission (rate frequency) fr and is expressed by Expression 2.

$$V\max = \frac{C \cdot fr}{4 fo \cos \xi} \qquad (2)$$

Here, C denotes sound velocity in an object, fo denotes central frequency of reception ultrasound, and ξ denotes an angle formed by a transmission direction of ultrasounds and a blood flow direction. When the Doppler frequency shift is greater than nyquist frequency, accurate measurement of blood flow velocity is not possible because of the aliasing occurred in a frequency spectrum of a Doppler signal.

That is, in order to improve the low flow velocity detection capability Vmin which is a first requirement of the colored Doppler method, it is necessary to set the rate frequency fr low or to increase the number of transmission performed in a predetermined direction. In order to improve the high flow velocity detection capability Vmax, it is necessary to set the rate frequency fr high. However, when the rate frequency fr is set high, a next ultrasound is emitted before reflected ultrasound from a deep portion is not received. Accordingly, there occurs a problem of a residual echo that reflected ultrasound corresponding to a preceded rate period are mixed and received.

The real time property which is a second requirement is determined by the number of images displayed per unit time (frame frequency) Fn. And the frame frequency Fn is expressed by Expression 3. Here, N is the total number of transmission/reception directions necessary for generating a colored Doppler image data. In order to improve the real time property, it is necessary to set the number of transmission/reception times L or the total number of transmission/reception directions N small.

$$Fn = \frac{fr}{L \cdot N} = \frac{1}{Tobs \cdot N} \propto \frac{V\min}{N} \qquad (3)$$

Moreover, in order to improve the spatial resolution which is a third requirement, it is necessary to increase the number of transmission/reception directions N. That is, the frame frequency Fn, the low flow velocity detection capability Vmin, the high flow velocity detection capability Vmax, and the spatial resolution have trade-off relations each other, and thus it is difficult to satisfy these requirements simultaneously. Therefore, the frame frequency Fn and the high flow velocity detection capability Vmax are important for the blood flow measurement in a circulatory organ, and the frame frequency Fn and the low flow velocity detection capability Vmin are important for the blood flow measurement in an abdomen or a peripheral organ.

In order to solve such a problem described above, a so-called simultaneous and parallel reception method for increasing the number of receiving signal per unit time by transmission ultrasound to a predetermined direction and simultaneously receiving reflected ultrasound in a plurality of directions adjacent to the predetermined direction is performed.

However, when the central axis of a transmitted ultrasonic beam and the central axis of a received ultrasonic beam are different in simultaneous and parallel reception method, the transmission/reception sensitivity is deteriorated. Moreover, when the number of reception directions for the simultaneous and parallel reception is three or more, it is difficult to obtain uniform transmission/reception sensitivity in a lateral direction (a direction perpendicular to the transmission/reception direction of the ultrasounds).

In order to solve such a problem, a method of reducing the number of transducer elements used for ultrasonic transmission or a method of enlarging the beam width of transmitting ultrasound by weighting the amplitudes of the driving signals supplied to the transducer elements in a array direction thereof is disclosed in, for example, Japanese Patent Publication (Kokai) No.3-155843.

On the other hand, a method of simultaneously performing transmission and reception of ultrasound in a plurality of directions is disclosed in U.S. Pat. No. 5,856,955. In this method, when the transmission ultrasound are transmission in a predetermined direction by driving a plurality of transducer elements with driving signals having predetermined delay time, the transmission of ultrasound in a plurality of directions is simultaneously performed by combining the driving signals having the delay time corresponding to a plurality of transmission directions and supplying the combined driving signal to the transducer elements.

In U.S. Pat. No. 5,856,955, the non-uniformity in transmission/reception sensitivity is improved by enlarging the beam width of the acoustic transmission field in comparison with the conventional case. However, as the focused transmitting ultrasound is used, it is difficult to enlarge the beam width so as to correspond to an acoustic reception field. Accordingly, distortion of the transmission and reception fields (hereinafter mentioned as the "beam distortion") or non-uniformity in transmission/reception sensitivity still remains.

FIG. 14 shows the beam distortion which is a first problem of the conventional method or the method disclosed in U.S. Pat. No. 5,856,955, and FIG. 15 shows the non-uniformity in transmission/reception sensitivity which is a second problem of the above-mentioned method.

FIG. 14A shows the simultaneous and parallel reception on the basis of an transmission field (solid line) and a plurality of acoustic reception fields (dotted lines) formed to overlap the acoustic transmission field when the transmission of ultrasounds is performed in a predetermined direction (central axis direction of the acoustic transmission field) by using a ultrasonic probe for convex-scanning in which the transducer elements are one-dimensionally arranged on a convex surface. In the figure, only the acoustic reception fields Br-1 and Br-3 corresponding to the sides of the acoustic transmission field Bt and the acoustic reception field Br-2 corresponding to the center of the acoustic transmission field Bt are shown for the purpose of simple description.

In the conventional simultaneous and parallel reception method, the transmission ultrasounds are focused at a predetermined position (depth) of the object, similarly to a non-simultaneous and parallel reception method, and ultrasonic energy is concentrated on the position. On the other hand, the reception ultrasound can form acoustic reception field continuously focused by applying a so-called dynamic focus method of sequentially moving focal point in the depth direction correspond to the reception time.

In this case, the transmission/reception sensitivity of ultrasound is determined by the product of an acoustic transmission field and an acoustic reception field (that is, an acoustic transmission/reception field). In the acoustic transmission/reception field formed by the acoustic transmission field Bt shown in FIG. 14A and the acoustic reception field (for example, the acoustic reception field Br-1) located at the side of the acoustic transmission field Bt, the acoustic transmission field in the focal area greatly affects the acoustic transmission/reception field. As a result, a beam distortion occurs in the central direction of the acoustic transmission/reception field as shown in FIG. 14B, and thus image distortion occurs in ultrasonic image data generated by the acoustic transmission/reception field Bo-1 or the acoustic transmission/reception field Bo-3 (not shown) having the beam distortion.

FIG. 15A schematically shows an acoustic transmission field pattern, an acoustic reception field pattern and an acoustic transmission/reception field pattern in the lateral direction of the simultaneous and parallel reception, where sound pressure at the side portion of the acoustic transmission field is smaller than that of the center. Accordingly, when the number of simultaneous reception directions is set to 3 or more, the amplitude of the acoustic transmission/reception field pattern (that is, transmission/reception sensitivity) is non-uniform in the lateral direction and dark and bright stripes are generated in the ultrasonic image data generated by the non-uniform transmission/reception field and deteriorates the image quality. The remarkable decrease in transmission/reception sensitivity at the side portion of the acoustic transmission field makes it difficult to estimate flow velocity, variance, etc in the colored Doppler image data, as well as image quality deterioration in the B mode image data.

When the acoustic transmission pattern is enlarged in the lateral direction as shown in FIG. 14B for the purpose of improvement in the non-uniform transmission/reception sensitivity, ultrasonic transmission energy is uselessly irradiated to areas not associated with generation of image data, thereby transmission/reception sensitivity is deteriorated and generation of a virtual images (artifacts) due to side lobes and multiple reflections increase.

That is, the beam distortion, the non-uniformity in transmission/reception sensitivity, and the decrease in transmission/reception sensitivity deteriorate the image quality of the ultrasonic image data and deteriorate diagnostic accuracy thereof.

On the other hand, when the acoustic transmission field for simultaneous and parallel reception is formed using the method disclosed in U.S. Pat. No. 5,856,955, it is necessary to combine a plurality of driving signals having delay times corresponding to a plurality of transmission directions, thereby causing a problem that the circuit configuration of a transmission unit is much complicated.

SUMMARY OF THE INVENTION

It is an object of the present invention to provide an ultrasonic diagnostic apparatus and an ultrasonic transmission method which decreases beam distortion of acoustic transmission/reception field and non-uniformity of transmission/reception sensitivity in simultaneous and parallel reception, using a simple circuit configuration.

To achieve the object, a first aspect of the present invention may provide an ultrasonic diagnostic apparatus including a transmission condition generation unit configured to generate a transmission condition to form an acoustic transmission field for simultaneous and parallel reception by combining the reference conditions, a transmission unit configured to transmit ultrasound to the object by driving the transducer elements based on the transmission condition and a reception unit configured to receive reflected ultrasound from a plurality of directions in the object simultaneously and in parallel in response to the transmission of the ultrasound.

a second aspect of the present invention may provide an ultrasonic transmission method including generating a transmission condition for simultaneous and parallel reception by combining reference conditions including at least one of delay time and driving amplitude for transmitting ultrasound to a plurality of directions, generating driving signals based on the transmission condition and forming an acoustic transmission field for simultaneous and parallel reception by driving a plurality of transducer elements with the driving signals.

In accordance with the aspect of the present invention, beam distortion of acoustic transmission/reception field or non-uniformity of transmission/reception sensitivity can be decreased with a simple circuit configuration. Accordingly, it is possible to generate ultrasonic image data showing a good real-time property and image quality so that diagnostic accuracy can be improved.

BRIEF DESCRIPTION OF THE DRAWINGS

Other object and features of the invention will become apparent to those skilled in the art as the disclosure is made in the following description of a preferred embodiment of the invention as illustrated in the accompanying sheet of drawings.

FIG. 6 is a diagram showing a method of generating transmission delay/amplitude conditions in the first embodiment shown in FIG. 1.

FIG. 14 is a diagram showing beam distortion of acoustic transmission/reception fields in the conventional simultaneous and parallel reception.

FIG. 15 is a diagram illustrating non-uniformity of transmission/reception sensitivity in the conventional simultaneous and parallel reception.

DETAILED DESCRIPTION OF THE INVENTION

In a first embodiment of the present invention described below, when simultaneous and parallel reception is performed using a convex scanning ultrasonic probe in which transducer elements are one-dimensionally arranged on a convex surface, an acoustic transmission field having uniform and suitable beam width in a lateral direction is formed by controlling delay time and driving amplitude of driving pulses (driving signals) supplied to a transmission transducer element group including a plurality of adjacent transducer elements.

In this case, the transmission conditions (transmission delay condition and transmission amplitude condition) for determining the delay time and the driving amplitude of driving pulses supplied to the transducer elements of the transmission transducer element group is set on the basis of the reference conditions (reference delay condition and reference amplitude condition) in a non-simultaneous and parallel reception using the transmission transducer element group.

Figure 1:
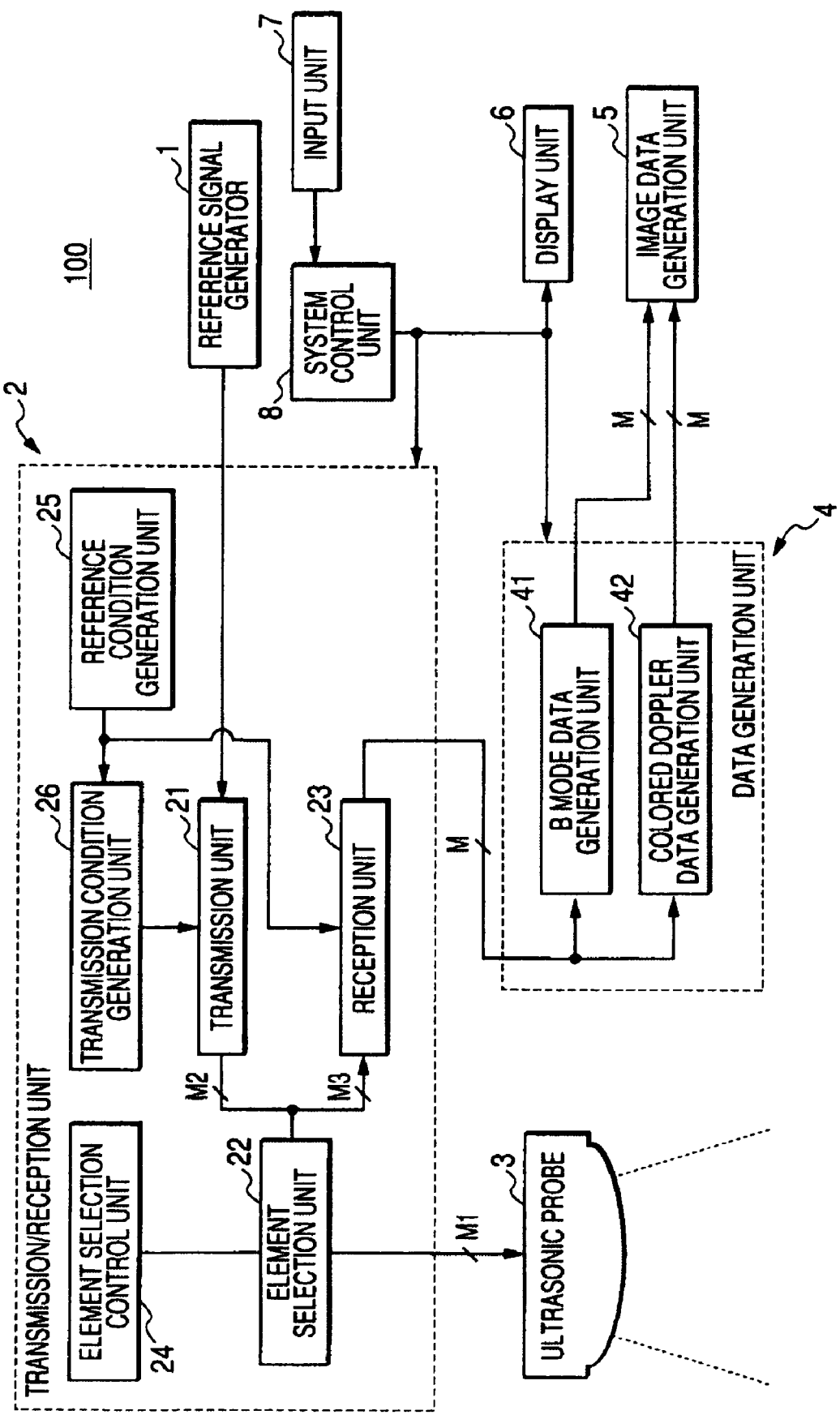
FIG. 1 is a block diagram showing an overall configuration of an ultrasonic diagnostic apparatus according to a first embodiment of the present invention.
Figure 2:
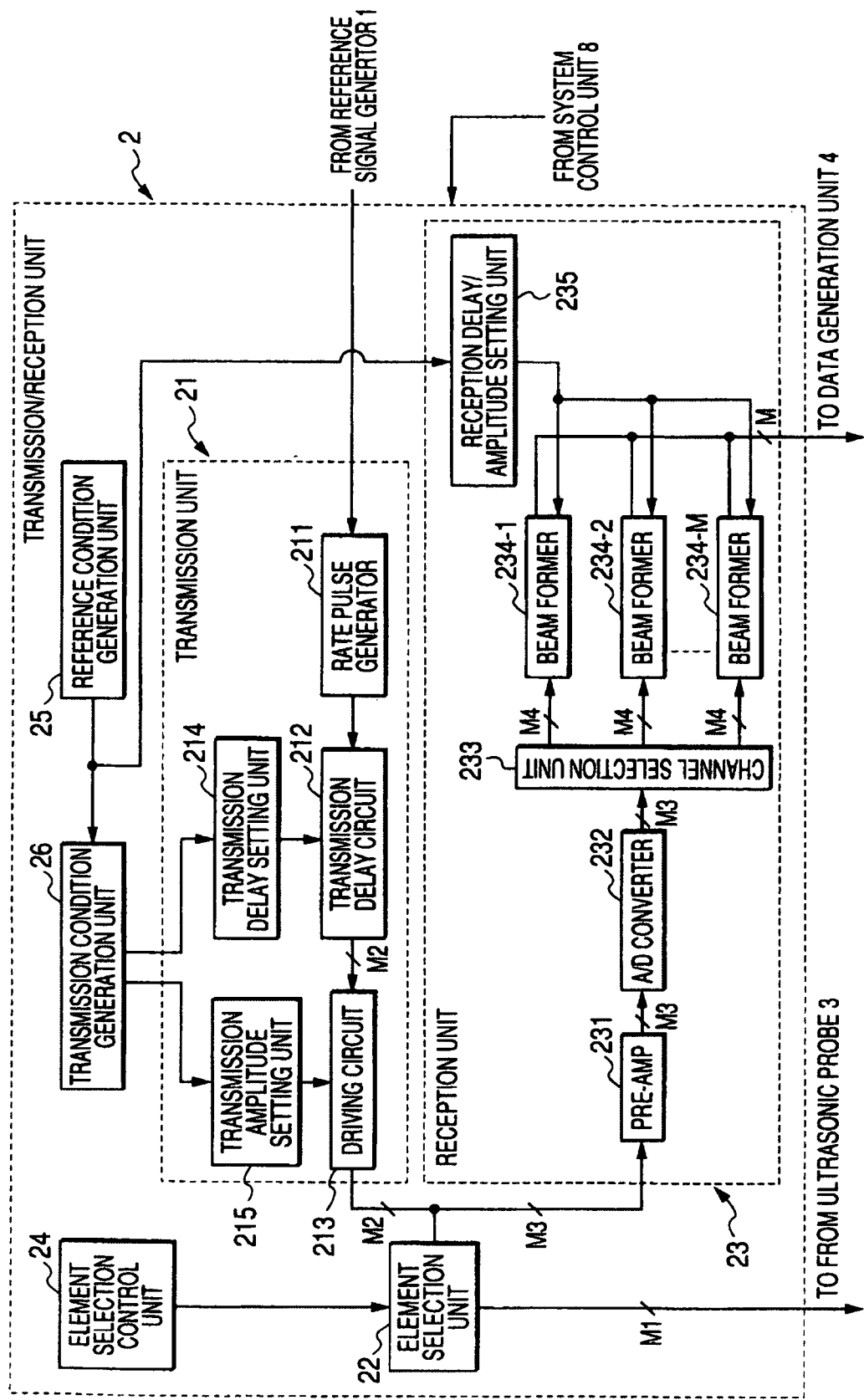
FIG. 2 is a block diagram showing a configuration of a transmission/reception unit in the first embodiment shown in FIG. 1.

The configuration and basic operations of the ultrasonic diagnostic apparatus according to the first embodiment of the present invention will be described below with FIG. 1 to FIG. 8. FIG. 1 is a block diagram showing the overall configuration of the ultrasonic diagnostic apparatus according to this embodiment. FIG. 2 and FIG. 8 are block diagrams showing a transmission/reception unit and a data generation unit constituting the ultrasonic diagnostic apparatus.

The ultrasonic diagnostic apparatus 100 shown in FIG. 1 includes a convex-scanning ultrasonic probe 3 which has a plurality of (M1) transducer elements arranged in one dimension on a convex surface and transmits ultrasound to and receives ultrasound from an object to be examined, a transmission/reception unit 2 which supplies driving pulses (driving signals) to M2 adjacent transducer elements (transmission transducer element group) selected among M1 transducer elements and which performs a phase-matching addition of reception signals obtained by simultaneous and parallel reception in M directions or non-simultaneous and parallel reception with M3 adjacent transducer elements (reception transducer element group) selected among the M1 transducer elements, a data generation unit 4 which processes the reception signals obtained from the transmission/reception unit 2 and generates B mode data and colored Doppler data, an image data generation unit 5 which stores the data generated from the data generation unit 4 and generates two-dimensional B mode image data and colored Doppler image data, and a display unit 6 which displays the obtained image data.

The ultrasonic diagnostic apparatus 100 further includes a reference signal generator 1 supplying a continuous wave or a rectangular wave having a frequency substantially equal to the central frequency of the transmission ultrasound to the transmission/reception unit 2 and the data generation unit 4, an input unit 7 which is used by an operator to, for example, input patient information, initial setting information of the apparatus, and a variety of command signals. And a system control unit 8 which systematically controls the respective units of the ultrasonic diagnostic apparatus 100 described above.

The ultrasonic probe 3 serves to perform transmission and reception of ultrasounds by bringing its front surface into contact with the surface of the object, and the M1 transducer elements are one-dimensionally arranged in a convex shape on the contact surface with the object. The transducer elements are electro-acoustic conversion elements and have a function of converting an electrical pulse (driving pulse) into an ultrasound pulse (transmission ultrasound) at the time of transmission and converting a reflected ultrasound (reception ultrasound) into an electrical signal (reception signal) at the time of reception.

The transmission/reception unit 2 shown in FIG. 2 includes a transmission unit 21 which generates driving pulses with predetermined delay time and driving amplitude to the M2 adjacent transducer elements selected among the M1 transducer elements in order to form an acoustic transmission field in the simultaneous and parallel reception or the non-simultaneous and parallel reception, a reception unit 23 which performs phase-matching adding (matching phases of the reception signals corresponding to the reflected ultrasound from a predetermined direction and adding the reception signals) of the reception signals obtained from the M3 adjacent transducer elements selected among the M1 transducer elements in order to form an acoustic reception field in the simultaneous and parallel reception or the non-simultaneous and parallel reception, an element selection unit 22 which selects transmission transducer elements and reception transducer elements among the M1 transducer elements and connects the selected transducer elements to the transmission unit 21 and the reception unit 23, and an element selection control unit 24 which controls the element selection unit 22.

Moreover, the transmission/reception unit 2 further includes a reference condition generation unit 25 which generates reference delay condition and reference amplitude condition for transmission and reference delay condition and reference amplitude condition for reception as reference conditions in the non-simultaneous and parallel reception, and a transmission condition generation unit 26 which generates a transmission delay condition and a transmission amplitude condition for the simultaneous and parallel reception as transmission conditions on the basis of the reference delay condition and the reference amplitude condition generated from the reference condition generation unit 25.

The transmission unit 21 includes a rate pulse generator 211, a transmission delay circuit 212, a driving circuit 213, a transmission delay setting unit 214, and a transmission amplitude setting unit 215.

The rate pulse generator 211 generates a rate pulse for determining a repetition period of transmission ultrasound by dividing the frequency of continuous waves supplied from the reference signal generator 1. The transmission delay circuit 212 having M2. channels gives transmission delay time for focusing the transmission ultrasound at a predetermined distance to the rate pulse on the basis of a delay control signal supplied from the transmission delay setting unit 214. The driving circuit 213 having M2 channels generates driving pulses synchronized with the rate pulse with predetermined delay time given by the transmission delay circuit 212 on the basis of an amplitude control signal supplied from the transmission amplitude setting unit 215.

On the other hand, the transmission delay setting unit 214 sets the transmission delay time of the transmission delay circuit 212 on the basis of the transmission delay condition generated by the transmission condition generation unit 26 of the transmission/reception unit 2. Similarly, the transmission amplitude setting unit 215 sets the driving amplitude of the driving circuit 213 on the basis of the transmission amplitude condition generated by the transmission condition generation unit 26.

The reception unit 23 includes a pre-amplifier 231 and an A/D converter 232 having M3 channels, a channel selection unit 233 and M-channel beam formers 234-1 to 234-M. The pre-amplifier 231 amplifies M3-channel reception signals supplied from the element selection unit 22 to get sufficient S/N. And a limiter circuit (not shown) for protecting the pre-amplifier 231 from high-voltage driving pulses generated from the driving circuit 213 of the transmission unit 21 is disposed at input portion of the pre-amplifier 231.

In order to perform the simultaneous and parallel reception in M directions, the channel selection unit 233 selects M4 adjacent channels among the M3 channels (M4<M3) in M positions, and supplies M reception signal groups corresponding to the M portion, each of which having M4 channel reception signals, to the beam former 234-1 to 234-M.

On the other hand, beam formers 234-1 to 234-M having delay circuits and an adder (not shown) set predetermined delay time and signal amplitude for focusing the reception ultrasound from predetermined depth to the M4-channel reception signals selected by the channel selection unit 233, and add the M4-channel reception signals.

In this case, the delay time and the signal amplitude are set on the basis of a delay control signal and an amplitude control signal supplied from a reception delay/amplitude setting unit 235 of the reception unit 23. However, the beam former 234-1 to 234-M are set delay time for so-called dynamic focusing, in which a focal area is sequentially shifted to deeper portion with reception time, thereby an acoustic reception field having a substantially uniform beam width without being dependent on the depth is formed.

The reception delay/amplitude setting unit 235 sets the delay time and the signal amplitude of the beam formers 234-1 to 234-M on the basis of the reference delay condition and the reference amplitude condition for reception which are generated by the reference condition generation unit 25 of the transmission/reception unit 2.

The element selection unit 22 of the transmission/reception unit 2 selects M2 adjacent transducer elements as a transmission transducer element group, and selects M3 adjacent transducer elements as a reception transducer element group among the M1 transducer elements disposed in the ultrasonic probe 3 on the basis of an element selection control signal supplied from the element selection control unit 24.

In this case, the selection of the transducer elements is performed so that the central position of the transmission transducer element group and the central position of the reception transducer element group are substantially in agreement.

On the other hand, the element selection control unit 24 supplies an element selection control signal to the element selection unit 22 for sequentially selecting the transmission transducer element group including the M2 transducer elements and the reception transducer element group including the M3 transducer elements at a rate period on the basis of a scanning control signal supplied from the system control unit 8.

Figure 3:
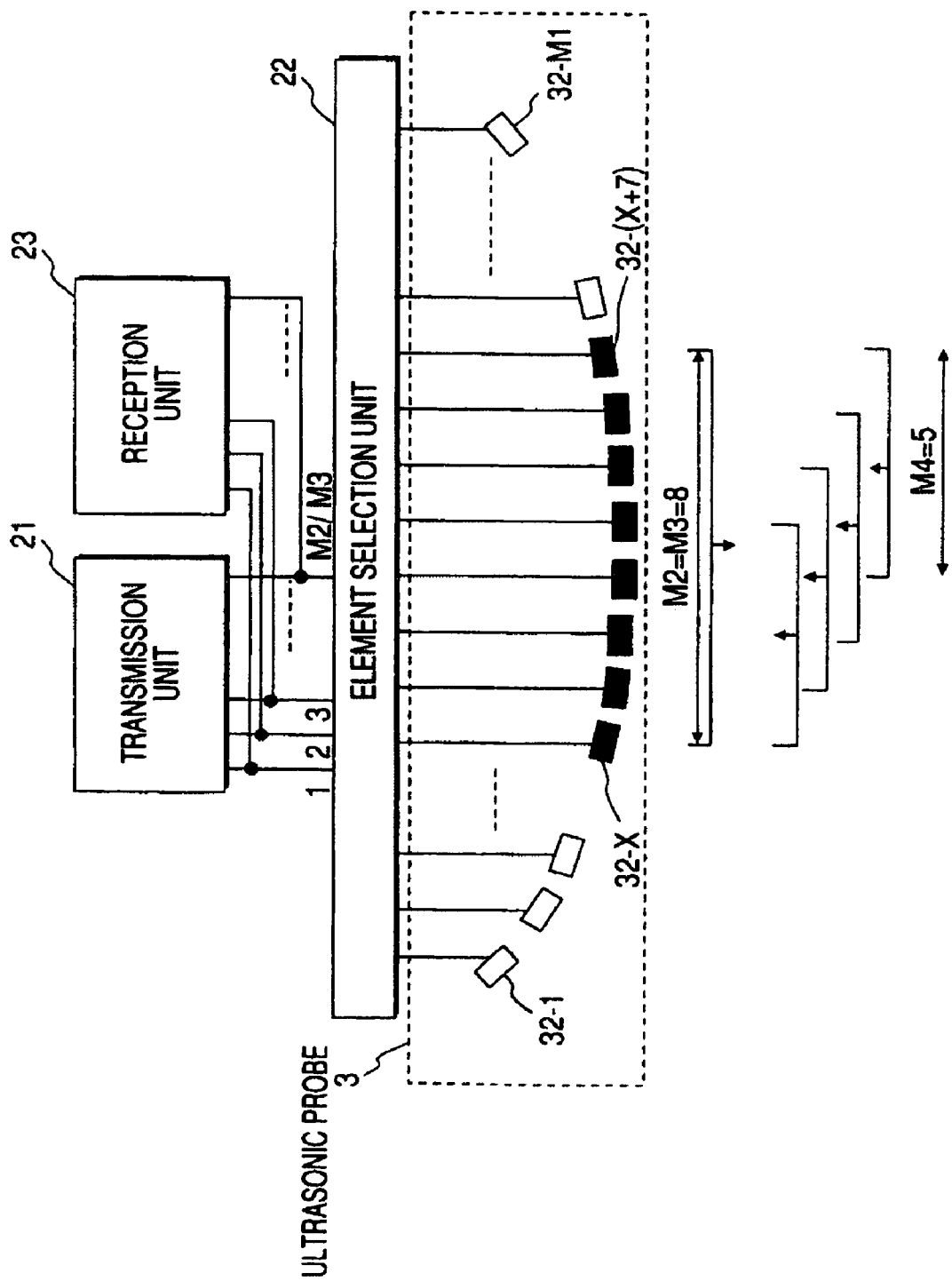
FIG. 3 is a schematic diagram showing a method of selecting a transmission transducer element group and a reception transducer element group in the simultaneous and parallel reception in the first embodiment shown in FIG. 1.

The selection of the transmission transducer element group and the reception transducer element group in the element selection unit 22 and the selection of the M-channel reception signal groups in the channel selection unit 233 are described in FIG. 3.

FIG. 3 is a schematic diagram showing a method of selecting the transmission transducer element group and the reception transducer element group for the simultaneous and parallel reception in adjacent M directions. For the purpose of simple description, the number of transducer elements M2 of the transmission transducer element group and the number of transducer elements M3 of the reception transducer element group are 8, the number of phase-matching addition channels M4 is 5, and the number of simultaneous and parallel receptions M is 4, but the invention is not limited to the numerals.

That is, when the simultaneous and parallel reception is performed in adjacent 4 directions (M=4) by using the convex-scanning ultrasonic probe 3 shown in FIG. 3, the element selection unit 22 selects the transducer elements 32-X to 32-(X+7) as the transmission transducer element group and the reception transducer element group among the transducer elements 32-1 to 32-M1 arranged on convex surface of the ultrasonic probe 3.

On the other hand, the channel selection unit 233 bundles 8-channel (M3=8) reception signals obtained from the transducer elements 32-X to 32-(X+7) into 4 (M=4) reception signal groups including 5-channel reception signals obtained from the transducer elements 32-X to 32-(X+4), the transducer elements 32-(X+1) to 32-(X+5), the transducer elements 32-(X+2) to 32-(X+6), and the transducer elements 32-(X+3) to 32-(X+7). The 5-channel reception signals of the respective reception signal groups are supplied to the beam former 234-1 to 234-M.

That is, the reception signals from the transducer elements 32-X to 32-(X+4) are supplied to the beam former 234-1, and the reception signals from the transducer elements 32-(X+1) to 32-(X+5), the reception signals from the transducer elements 32-(X+2) to 32-(X+6), and the reception signals from the transducer elements 32-(X+3) to 32-(X+7) are supplied to the beam former 234-2 to 234-4, respectively. The respective beam formers 234-1 to 234-M set the delay time and the signal amplitude for the dynamic focusing to the M4-channel reception signals selected by the channel selection unit 233 and add the M4-channel reception signals on the basis of the delay control signal and the amplitude control signal supplied from the reception delay/amplitude setting unit 235. Then, 4 (M=4) acoustic reception fields are formed by the phase-matching addition process.

By the transmission and reception described above, 4 acoustic reception fields are formed so as to overlap the acoustic transmission fields formed by the transducer element group including the transducer elements 32-X to 32-(X+7). Accordingly, the simultaneous and parallel reception in 4 directions is performed.

Here, the transmission direction and the reception direction of ultrasound are set substantially perpendicular to the array surface of the transducer elements, but the transmission direction and the reception direction may be set to any direction by allowing the transmission delay circuit 212 or the beam former 234 to set deflection delay time. However, in any case, the acoustic reception field is formed to overlap the acoustic transmission field in the simultaneous and parallel reception according to the first embodiment.

Referring back to FIG. 1, the reference condition generation unit 25 of the transmission/reception unit 2 generates the reference delay condition and the reference amplitude condition for transmission and the reference delay condition and the reference amplitude condition for reception in the non-simultaneous and parallel reception in which image data are generated based on the acoustic transmission field and the acoustic reception field, the central axis of which is substantially coincident with the central axis of the acoustic transmission field.

Figure 4:
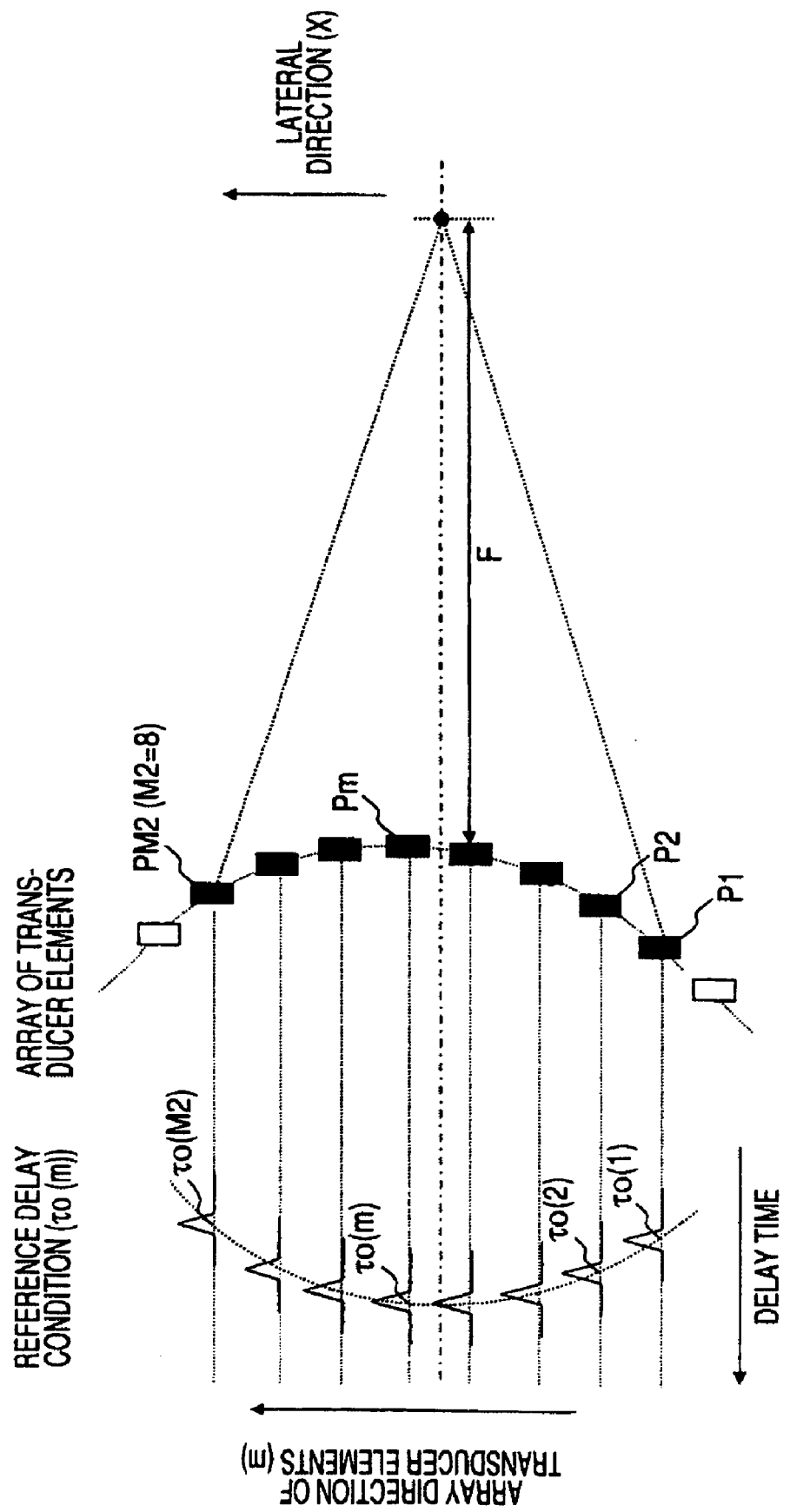
FIG. 4 is a schematic diagram showing a reference delay condition for transmission corresponding to the transducer elements in the first embodiment shown in FIG. 1.

FIG. 4 is a schematic diagram showing a reference delay conditions $\tau o(m)$ for transducer elements Pm (where m is 1 to M2 (M2=8)) when an ultrasonic beam is focused at a distance F using the M2 transducer elements as the transmission transducer element group and the reception transducer element group, where the transducer elements P1 to PM2 correspond to the transducer elements 32-X to 32-(X+7) shown in FIG. 3. Here, when the dynamic focusing is performed for the reception, the reference condition generation unit 25 generates the reference delay condition for focusing the ultrasound at a plurality of distances.

Figure 5B:
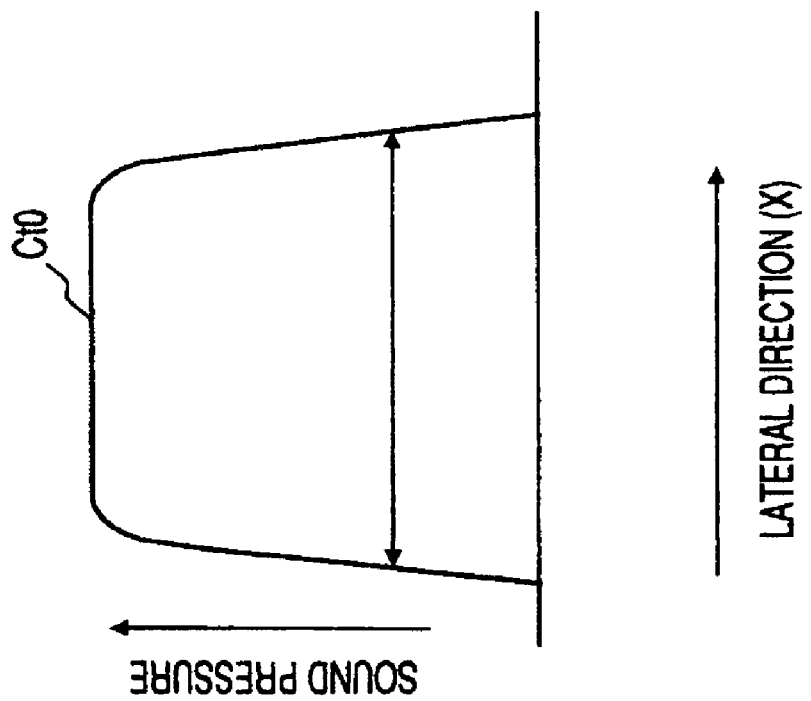
FIG. 5 is a diagram showing the reference amplitude condition for transmission corresponding to the transducer elements and an acoustic transmission field generated by driving pulses based on the reference amplitude condition in the first embodiment shown in FIG. 1.
Figure 5A:
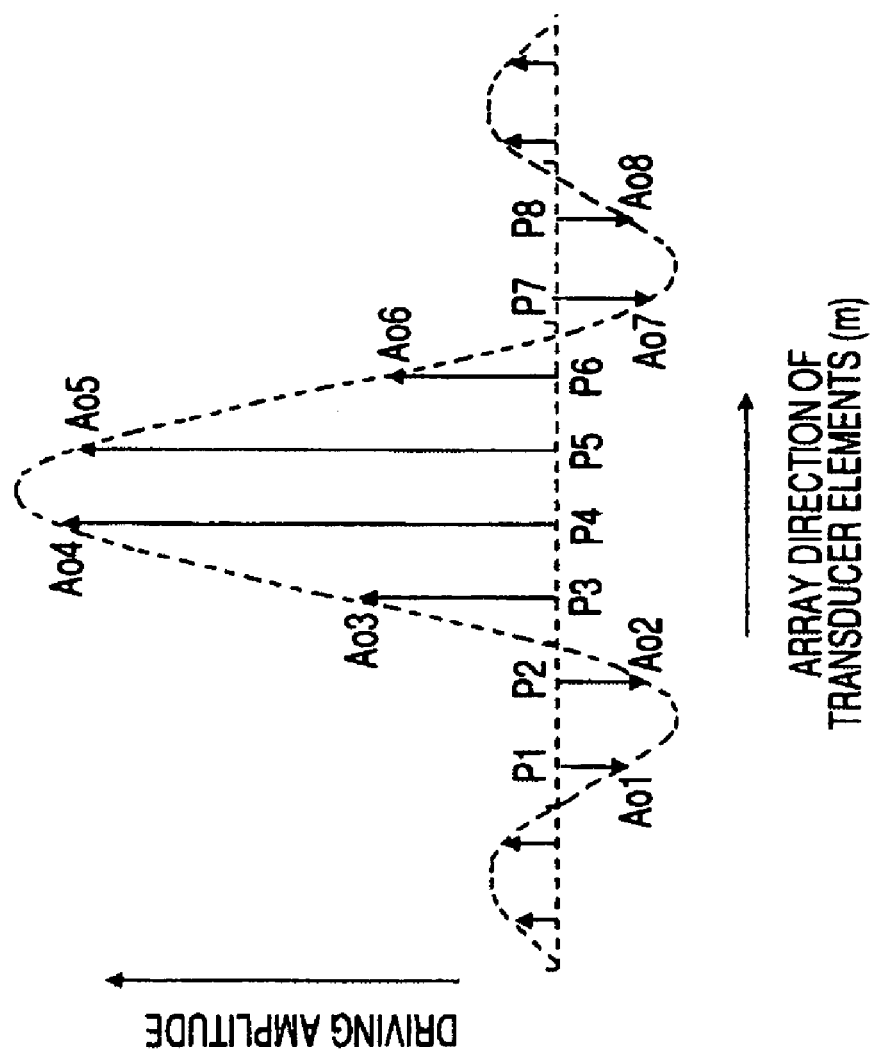

On the other hand, FIG. 5 shows a reference amplitude conditions Ao(m) (FIG. 5A) for transmission corresponding to the transducer elements Pm (where m is 1 to M2) when the acoustic transmission field is formed using M2 (M2=8) transducer elements and an acoustic transmission field Ct0 (FIG. 5B) generated by using driving pulses with driving amplitude based on the reference amplitude conditions Ao(m). In this case, the reference condition generation unit 25 generates the reference amplitude condition Ao(m) for driving the m-th transducer element Pm, for example, on the basis of an Sinc function shown in FIG. 5A.

When the transducer elements Pm are driven by the driving pulses based on the reference amplitude condition Ao(m) for transmission expressed by the Sinc function and the reference delay conditions $\tau o(m)$, the rectangular acoustic transmission field Ct0 shown in FIG. 5B is formed in the focal area. Note that, the reference amplitude condition describe above is generally generated based on uniform distribution function or Hamming function.

Next, the function of the transmission condition generation unit 26 which is the most important function in the first embodiment will be schematically described with reference to FIGS. 6 and 7. In the following description, the transmission delay condition $\tau(m)$ and the transmission amplitude condition A(m) for forming an acoustic transmission field having a beam width and uniform intensity suitable for the simultaneous and parallel reception are formed by using two transmission reference delay conditions $\tau o(m-\Delta M)$ and $\tau o(m+\Delta M)$ and two transmission reference amplitude conditions $Ao(m-\Delta M)$ and $Ao(m+\Delta M)$ which are shifted in the array direction of the transducer elements by $-\Delta M$ and $+\Delta M$ (for example, $\Delta M=1$).

The acoustic transmission field formed by the driving pulses based on the reference delay condition for transmission $\tau o(m)$ shown in FIG. 4 and the reference amplitude condition for transmission Ao(m) shown in FIG. 5 cannot generally have a wide beam width required for the simultaneous and parallel reception. Accordingly, as shown in FIG. 6, third driving pulse group PL3 are generated by combining a first driving pulse group PL1 obtained by shifting a reference driving pulse group PL0 based on the reference delay condition for transmission τo(m) and the reference amplitude condition for transmission Ao(m) in the array direction of the transducer elements by −ΔM and a second driving pulse group PL2 obtained by shifting the reference driving pulse group PL0 by +ΔM. By driving the transducer elements Pm (where m is 1 to M2) with the third driving pulse group PL3, an acoustic transmission field Ct3 having uniform intensity and a suitable beam width shown in FIG. 7, is formed. The acoustic transmission field Ct3 is obtained by shifting the acoustic transmission field Ct0 resulting from the reference driving pulse group PL0 shown in FIG. 5B by ±ΔM and combining them.

That is, the acoustic transmission field Ct3 is formed so that an end of the acoustic transmission field Ct1 resulting from the first driving pulse group PL1 and an end of the acoustic transmission field Ct2 resulting from the second driving pulse group PL2 overlap each other in the focal area. At this time, the desired acoustic transmission field Ct3 having a beam width BW3 which is about double the beam width BW1 of the acoustic transmission field Ct1 or the beam width BW2 of the acoustic transmission field Bt2 and being uniform in which the end is rapidly attenuated is formed by setting the distance 2ΔM between the centers of the first driving pulse group PL1 and the second driving pulse group PL2 to proper value.

The formation of the acoustic transmission field Ct3 by combining the first driving pulse group PL1 and the second driving pulse group PL2 can be realized by the technique described in U.S. Pat. No. 5,856,955, but as described above, this method has a problem that the circuit configuration of the transmission unit 21 is much complicated.

In the first embodiment, an acoustic transmission field substantially equivalent to the acoustic transmission field Ct3 obtained by combining two -driving pulse groups PL1 and PL2 are generated by controlling the delay time and the driving amplitude of a single driving pulse group. Next, a method of generating the transmission delay condition τ(m) and the transmission amplitude condition A(m) generated by the transmission condition generation unit 26 on the basis of the reference delay condition τo(m) and the reference amplitude condition Ao(m) for transmission generated by the reference condition generation unit 25 will be described.

In this case, Ho(m) assumed to be the reference driving pulse of a transducer element Pm based on the reference delay condition To(m) and the reference amplitude condition Ao(m), the driving pulse H(m) based on the transmission delay condition τ(m) and the transmission amplitude condition A(m) generated by the transmission condition generation unit 26 can be expressed by Expression 4. Here, W(t) and Wo(t) denote envelope functions of the driving pulse H(m) and the reference driving pulse Ho(m).

$$H(m) = \qquad (4)$$
$$A(m)W\{t-\tau(m)\}\exp\{j\omega(t-\tau(m)\} = Ho(m-\Delta M) + Ho(m+\Delta M) =$$
$$Ao(m-\Delta M)Wo\{t-\tau o(m-\Delta M)\}\exp[j\omega\{t-\tau o(m-\Delta M)\}] +$$
$$Ao(m+\Delta M)Wo\{t-\tau o(m+\Delta M)\}\exp[j\omega\{t-\tau o(m+\Delta M)\}]$$

Here, generally, ΔM<<M2 is satisfied, and when the period of envelope function is much longer than the period of the driving pulse (that is, the reciprocal of an ultrasonic central frequency), Expression 5 is satisfied approximately.

$$Ao(m-\Delta M) \approx Ao(m+\Delta M) \approx Ao(m) \qquad (5)$$
$$Wo\{t-\tau o(m-\Delta M)\} \approx Wo\{t-\tau o(m+\Delta M)\} \approx Wo\{t-\tau o(m)\}$$

Accordingly, the transmission delay condition τ(m) and the transmission amplitude condition A(m) of the driving pulse H(m) can be expressed by Expression 6 applying the reference delay condition τo(m) and the reference amplitude condition Ao(m) of the reference driving pulse Ho(m).

$$H(m) = Ao(m)Wo\{t-\tau o(m)\}[ \qquad (6)$$
$$\exp\{j\omega(t-\tau o(m-\Delta M))\} + \exp\{j\omega(t-\tau o(m+\Delta M))\}] =$$
$$A(m)W\{t-\tau(m)\}\exp[j\omega\{t-\tau(m)\}]$$
$$A(m) = 2Ao(m)[\cos\{(\omega\tau o(m-\Delta M) - \omega\tau o(m+\Delta M))/2\}]$$
$$W\{t-\tau(m)\} \approx Wo\{t-\tau o(m)\}$$
$$\tau(m) = \frac{\tau o(m-\Delta M) + \tau o(m+\Delta M)}{2}$$

As described above, the acoustic transmission field substantially equivalent to the acoustic transmission field (see FIG. 7) obtained by combining the first driving pulse group PL1 and the second driving pulse group PL2 (see FIG. 6) can be obtained by driving the transducer elements P1 to PM2 using the driving pulse H(m) based on the transmission delay condition τ(m) and the transmission amplitude condition A(m) obtained from Expression 6.

That is, the transmission condition generation unit 26 generates the transmission delay condition τ(m) and the transmission amplitude condition A(m) on the basis of the calculation using the reference delay condition τo(m) and the reference amplitude condition Ao(m) for transmission supplied from the reference condition generation unit 25, and supplies these conditions to the transmission delay setting unit 214 and the transmission amplitude setting unit 215 of the transmission unit 21. The transmission delay setting unit 214 and the transmission amplitude setting unit 215 set the delay time of the transmission delay circuit 212 and the driving amplitude of the driving circuit 213 on the basis of the transmission delay condition τ(m) and the transmission amplitude condition A(m) as described above.

The data generation unit 4 shown in FIG. 1 includes a B mode data generation unit 41 for generating B mode data by processing M-channel reception signals output from the beam formers 234-1 to 234-M of the reception unit 23 and a colored Doppler data generation unit 42 for generating colored Doppler data by processing the reception signals.

The B mode data generation unit 41 of the data generation unit 4 shown in FIG. 8 includes an envelope detector 411 and a logarithmic converter 412. The envelope detector 411 detects an envelope of the M-channel reception signals output from the beam former 234-1 to 234-M in the reception unit 23 of the transmission/reception unit 2. The logarithmic converter 412 relatively emphasizes small signal amplitude by logarithmic conversion process for the reception signal after envelope detection h and generates the B mode data corresponding to the M directions of simultaneous and parallel reception.

On the other hand, the colored Doppler data generation unit 42 of the data generation unit 4 includes a π/2 phase shifter 421, mixers 422-1 and 422-2, and low pass filters (LPF) 423-1 and 423-2, and generates complex signals (I signal and Q signal) by detecting an quadrature phase from the M-channel reception signals supplied from the reception unit 23 of the transmission/reception unit 2.

The colored Doppler data generation unit 42 includes a Doppler signal memory 424, an MTI filter 425, and an autocorrelation calculation unit 426. The complex signals obtained by the detection of the quadrature phase are stored in the Doppler signal memory 424. Subsequently, the MTI filter 425 which is a digital high pass filter reads out the complex signals stored in the Doppler signal memory 424 and removes Doppler components (clutter components) resulting from fixed reflective objects in organ or a respiratory movement or a pulsatile movement of the reflective objects in the organ from the complex signals. The autocorrelation calculation unit 426 calculates an autocorrelation value of the complex signals extracted by the MTI filter 425 and calculates an average flow velocity, variance, and power of the blood flow on the basis of the autocorrelation value, thereby generating colored Doppler data corresponding to the M directions of simultaneous and parallel reception.

Referring to FIG. 1 again, the image data generation unit 5 sequentially stores the B mode data and the colored Doppler data generated in the unit of M rasters by the data generation unit 4 and generates two-dimensional B mode image data and two-dimensional colored Doppler image data.

The display unit 6 includes a display data generation circuit, a conversion circuit, and a monitor, which are not shown. The display data generation circuit generates display data by performing a scanning conversion process corresponding to a predetermined display format to the B mode image data or the colored Doppler image data generated from the image data generation unit 5. The conversion circuit performs a D/A conversion and a television format conversion to the display data and displays the converted display data on the monitor.

The input unit 7 includes input devices such as a display panel or a keyboard, a track ball, a mouse, selection buttons, and input buttons on an operation panel, which are not shown, and is used to input patient information, set data collection conditions and display condition, input various command signals, etc.

Specifically, in the first embodiment, the input unit 7 performs the setting of the number of transducer elements M2 of the transmission transducer element group, the number of transducer elements M3 of the reception transducer element group, the number of channels M4 of the phase-matching addition, the number of directions M for simultaneous and parallel reception, the combination interval ΔM of the acoustic transmission field, the selection of the reference amplitude condition and the simultaneous and parallel reception/non-simultaneous and parallel reception mode. However, the numbers of transmission transducer elements and reception transducer elements or the weighting condition may be set on the basis of information on the ultrasonic probe 3 (for example, probe ID) and information on the number of directions M for simultaneous and parallel reception.

The system control unit 8 includes a CPU and a storage circuit, (not shown). And a variety of information is input or set through the input unit 7 by an operator are stored in the storage circuit. The CPU systematically controls the transmission/reception unit 2, the data generation unit 4, the image data generation unit 5, and the overall system on the basis of the information.

The system control unit 8 supplies control signals to the element selection control unit 24 and the reception unit 23 of the transmission/reception unit 2, and performs the control for the simultaneous and parallel reception in M directions of the acoustic transmission field formed by the transmission transducer elements and the control for convex scanning to the object by sequentially shifting the transmission transducer elements and the reception transducer elements in the array direction of the transducer elements.

A procedure of generating image data in a simultaneous and parallel reception mode according to the first embodiment will be described with reference to FIG. 9. Here, for the purpose of easy description, it is assumed that the number of transducer elements M2 of the transmission transducer element group and the number of transducer elements M3 of the reception transducer element group are equal to each other, but the invention is not limited to the assumption.

The operator of the ultrasonic diagnostic apparatus 100 sets the probe ID of the ultrasonic probe 3 and the conditions necessary for collecting image data through the input unit 7 shown in FIG. 1, and stores the information in a storage circuit in the system control unit 8. The initial setting conditions include the numbers of transducer elements M2 of the transmission transducer element group and the reception transducer element group, the number of channels M4 for the phase-matching addition, the number of directions M for the simultaneous and parallel reception, and the combination interval ΔM of the acoustic transmission field, and a reference amplitude condition (S1 in FIG. 9).

When the initial setting is finished, the operator selects the simultaneous and parallel reception mode through the input unit 7 and then starts the transmission and reception of ultrasound by fixing the end (ultrasonic transmission and reception surface) of the ultrasonic probe 3 to a predetermined position on the surface of the object. At this time, the system control unit 8 supplies the information on the number of transducer elements M2 of the transmission transducer element group and the reception transducer element group stored in the storage circuit to the element selection control unit 24, the transmission condition generation unit 26, and the reference condition generation unit 25 of the transmission/reception unit 2, supplies the information on the number of channels M4 of the reception signal group for the phase-matching addition, the number M for the simultaneous and parallel reception to the channel selection unit 23 of the reception unit 23, supplies the combination interval ΔM of the acoustic transmission field to the transmission condition generation unit 26, supplies the information on the selection of the reference amplitude condition to the reference condition generation unit 25, and stores the information described above in the storage circuits of the respective units.

Figure 9:
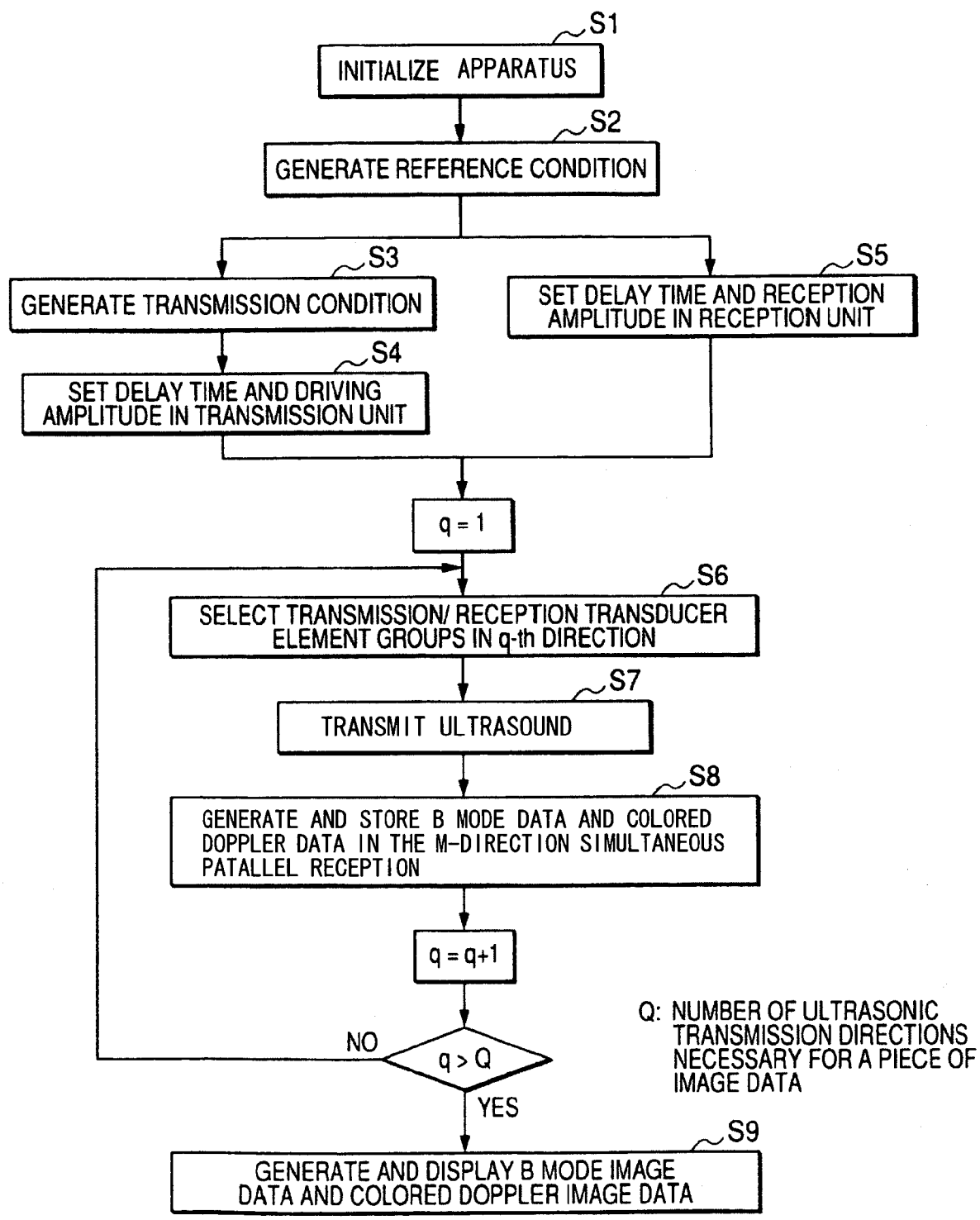
FIG. 9 is a flowchart illustrating a procedure in which image data are generated in the first embodiment shown in FIG. 1.

The reference condition generation unit 25 of the transmission/reception unit 2 generates the reference delay condition $\tau o(m)$ and the reference amplitude condition $Ao(m)$ for transmission on the basis of the information on the number of transducer elements M2 of the transmission transducer element group and the reception transducer element group and the information on the selection of the reference amplitude condition supplied from the system control unit 8, and then supplies these conditions to the transmission condition generation unit 26 (S2 in FIG. 9).

The transmission condition generation unit 26 generates the transmission delay condition $\tau(m)$ and the transmission amplitude condition $A(m)$ by substituting the reference delay condition $\tau o(m)$ and the reference amplitude condition $Ao(m)$ supplied from the reference condition generation unit 25 and the combination interval ΔM of the acoustic transmission field stored in its own storage circuit for, for example, Expression 6 (S3 in FIG. 9).

Next, the transmission condition generation unit 26 supplies the transmission delay condition $\tau(m)$ to the transmission delay setting unit 214 and supplies the transmission amplitude condition A(m) to the transmission amplitude setting unit 215. The transmission delay setting unit 214 and the transmission amplitude setting unit 215 set the delay time of the transmission delay circuit 212 and the driving amplitude of the driving circuit 213 on the basis of the condition information (S4 in FIG. 9).

On the other hand, the reception delay/amplitude setting unit 235 of the reception unit 23 set the delay time and the amplitude of the beam formers 234-1 to 234-M for reception on the basis of the reference delay condition and the reference amplitude condition for reception supplied from the reference condition generation unit 25 (S5 in FIG. 9).

Next, in the ultrasonic transmission and reception in the first direction (q=1), the element selection control unit 24 supplies a control signal to a multiplexer not shown in the element selection unit 22 on the basis of the information on the numbers of transducer elements M2 for transmission and reception supplied from the system control unit 8. The element selection unit 22 selects the transducer elements 32-1 to 32-M2 to be used for the ultrasonic transmission and reception in the first direction (S6 in FIG. 9).

On the other hand, the rate pulse generator 211 shown in FIG. 2 generates rate pulses for determining the repetition period of the ultrasound pulses by dividing the frequency of a reference signal supplied from the reference signal generator 1 and supplies the rate pulses to the transmission delay circuit 212. The transmission delay circuit 212 with M channels gives the delay time set by the transmission delay setting unit 214 to the rate pulses and supplies the rate pulses to the driving circuit 213.

The driving circuit 213 generates the driving pulses which has the driving amplitude set by the transmission amplitude setting unit 215 and has the delay time synchronized with the rate pulses supplied from the transmission delay circuit 212, supplies the driving pulses to the transducer elements 32-1 to 32-M2 selected by the element selection unit 22 and transmits the ultrasound to the object (S7 in FIG. 9).

The transmission ultrasound irradiated to the object by driving the transducer elements 32-1 to 32-M2 is partially reflected at the boundary surfaces between organs or tissues having different acoustic impedance. Furthermore, the frequency of ultrasound is Doppler-shifted when the ultrasound is reflected at the moving reflectors such as cardiac wall or blood cells.

The reflected ultrasound (reception ultrasound) from tissues or blood cells in the object is received by the transducer elements 32-1 to 32-M2 selected by the element selection unit 22 and converted into electrical signals (reception signals). The reception signals are supplied to the reception unit 23 through the element selection unit 22, amplified into a predetermined magnitude by the pre-amplifier 231 and converted into digital signals by the A/D converter 232.

The M2 channel reception signals converted into the digital signals are supplied to the channel selection unit 233. The channel selection unit 233 selects M reception signal groups with M4 adjacent channels among the M2 channel reception signals (M4<M2), and supplies the M reception signal groups to the M-channel beam formers 234-1 to 234-M.

That is, the reception signals obtained from the transducer elements 32-1 to 32-M4 are supplied to the beam former 234-1, and reception signals obtained from the transducer elements 32-2 to 32-(M4+1) are supplied to the beam former 234-2. Similarly, the reception signal obtained from the transducer elements 32-3 to 32-(M4+2) and the transducer elements 32-4 to 32-(M4+3) are supplied to the beam former 234-3 and the beam former 234-4, respectively. The respective beam formers 234-1 to 234-M perform the phase-matching addition to the M4-channel reception signals and perform the dynamic focusing.

The M-channel reception signals obtained by the phase-matching addition in the beam formers 234-1 to 234-M are supplied to the B mode data generation unit 41 of the data generation unit 4 shown in FIG. 8, subjected to the envelope detection and the logarithmic conversion, and stored in the B mode data storage area of the image data generation unit 5 shown in FIG. 1.

On the other hand, at the time of the generation of the colored Doppler data in the first transmission direction, Doppler signals are detected from the reception signals obtained by continuous ultrasonic transmission and reception in the transmission direction using the transducer elements 32-1 to 32-M2, That is, the system control unit 8 controls the element selection control unit 24 to select the transducer elements 32-1 to 32-M2 and to perform the ultrasonic transmission and reception for color Doppler. The obtained M-channel reception signals are supplied to the colored Doppler data generation unit 42 of the data generation unit 4 shown in FIG. 8, and complex signals are generated on the basis of the quadrature phase detection using the mixers 422-1 and 422-2 and the LPFs 423-1 and 423-2.

Next, the real components (I components) and the imaginary components (Q components) of the complex signals are stored in the Doppler signal memory 424. Similarly, the complex signals are collected from the reception signals obtained by the 2-nd to L-th ultrasonic transmission and reception using the same transducer element group and are stored in the Doppler signal memory 424.

When the storing of the M-channel complex signals obtained by the L-th ultrasonic transmission and reception using the transducer elements 32-1 to 32-M2 is finished, the system control unit 8 sequentially reads out L complex signal components corresponding to a predetermined position (depth) from the M-channel complex signals stored in the Doppler signal memory 424 and supplies the L complex signal components to the MTI filter 425. The MTI filter 425 performs a filtering process to the complex signal components and extracts Doppler components resulting from the blood flow (blood flow components) by excluding the Doppler components resulting from the fixed reflector (clutter components)

The autocorrelation calculation unit 426 to which the complex signals with the blood flow component are supplied from the MTI filter 425 performs an autocorrelation process using the complex signals, and calculates the average velocity, the variance and the power of the blood flow on the basis of the autocorrelation result. The autocorrelation calculation unit 426 performs the calculation to other positions (depths) and stores the calculated average velocity, variance and power of the blood flow in the color Doppler data storage area of the image data generation unit 5 shown in FIG. 1.

That is, in the B mode data storage area and the colored Doppler data storage area of the image data generation unit 5, the B mode data and the colored Doppler data in the M directions of the simultaneous and parallel reception corresponding to the first transmission direction (S8 in FIG. 9).

In the same procedure, the system control unit 8 controls the element selection control unit 24 to repeat the ultrasonic transmission in the second direction (q=2) by using the transducer elements 32-(M2+1) to 32-2M2, the ultrasonic transmission in the third direction (q=3) using the transducer elements 32-(2M2+1) to 32-3M2, . . . , the ultrasonic transmission in the Q-th direction (q=Q). The B mode data and the colored Doppler data obtained by the simultaneous and parallel reception in the respective ultrasonic transmission directions are stored in the B mode data storage area and the colored Doppler data storage area of the image data generation unit 5 (S6 to S8 in FIG. 9).

Through the procedure mentioned above, the B mode data and the colored Doppler data obtained in the M directions for each of the first to Q-th transmission directions are sequentially stored in the image data generation unit 5, and then two-dimensional or three-dimensional B mode image data and colored Doppler image data are generated there from. The display data generation circuit of the display unit 6 generates display data by performing a scanning conversion process corresponding to a predetermined display format to the B mode image data and the colored Doppler image data generated from the image data generation unit 5. The display data are subjected to the D/A conversion and the television format conversion in the conversion circuit and then displayed on the monitor (S9 in FIG. 9).

According to the first embodiment described above, when the simultaneous and parallel reception is performed to a diagnostic area of an object by using the convex scanning ultrasonic probe, the beam distortion in the acoustic transmission/reception field in the simultaneous and parallel reception or the non-uniformity of transmission/reception sensitivity in the respective directions of the parallel reception can be reduced with a simple circuit configuration.

In the first embodiment, it is possible to the acoustic transmission field having excellent uniformity and a rapid attenuation characteristic at the sides thereof by using the reference amplitude condition based on the Sinc function. Accordingly, since the transmission ultrasound is only irradiated to the area where the simultaneous and parallel reception is performed, it is possible to use the transmission energy effectively, reduce the side lobe or the artifact due to multiple reflections, and generate image data excellent in sensitivity.

That is, according to the first embodiment, since a uniform acoustic transmission field can be formed in a wide area, it is possible to increase the number of directions for the simultaneous and parallel reception and thus to generate image data with excellent temporal resolution, spatial resolution, and detection capability. Since the transmission unit forming the acoustic transmission field described above can be embodied with a simple circuit configuration, it is possible to provide the ultrasonic diagnostic apparatus and the ultrasound transmitting method excellent in cost performance.

A second embodiment of the present invention will be described bellow. In the second embodiment, when the simultaneous and parallel reception is performed using a sector-scanning ultrasonic probe in which the transducer elements are linearly arranged in one dimension, an acoustic transmission field having a uniform and suitable beam width in the lateral direction is formed by controlling the delay time and the driving amplitude of the driving pulses to the transmission transducer element group including a plurality of adjacent transducer elements.

In this case, similarly to the first embodiment, the transmission conditions (transmission delay condition and transmission amplitude condition) for determining the delay time and the driving amplitude of the driving pulses to the transducer elements of the transmission transducer element group are set on the basis of the reference transmission conditions (reference delay condition and reference amplitude condition) in the non-simultaneous and parallel reception using the transmission transducer element group.

The ultrasonic diagnostic apparatus according to the second embodiment of the present invention is different from the ultrasonic diagnostic apparatus according to the first embodiment, in the configurations of the ultrasonic probe and the transmission/reception unit. The configuration and the basic operations of the ultrasonic diagnostic apparatus according to the second embodiment will be described with reference to FIGS. 10 to 12.

Figure 10:
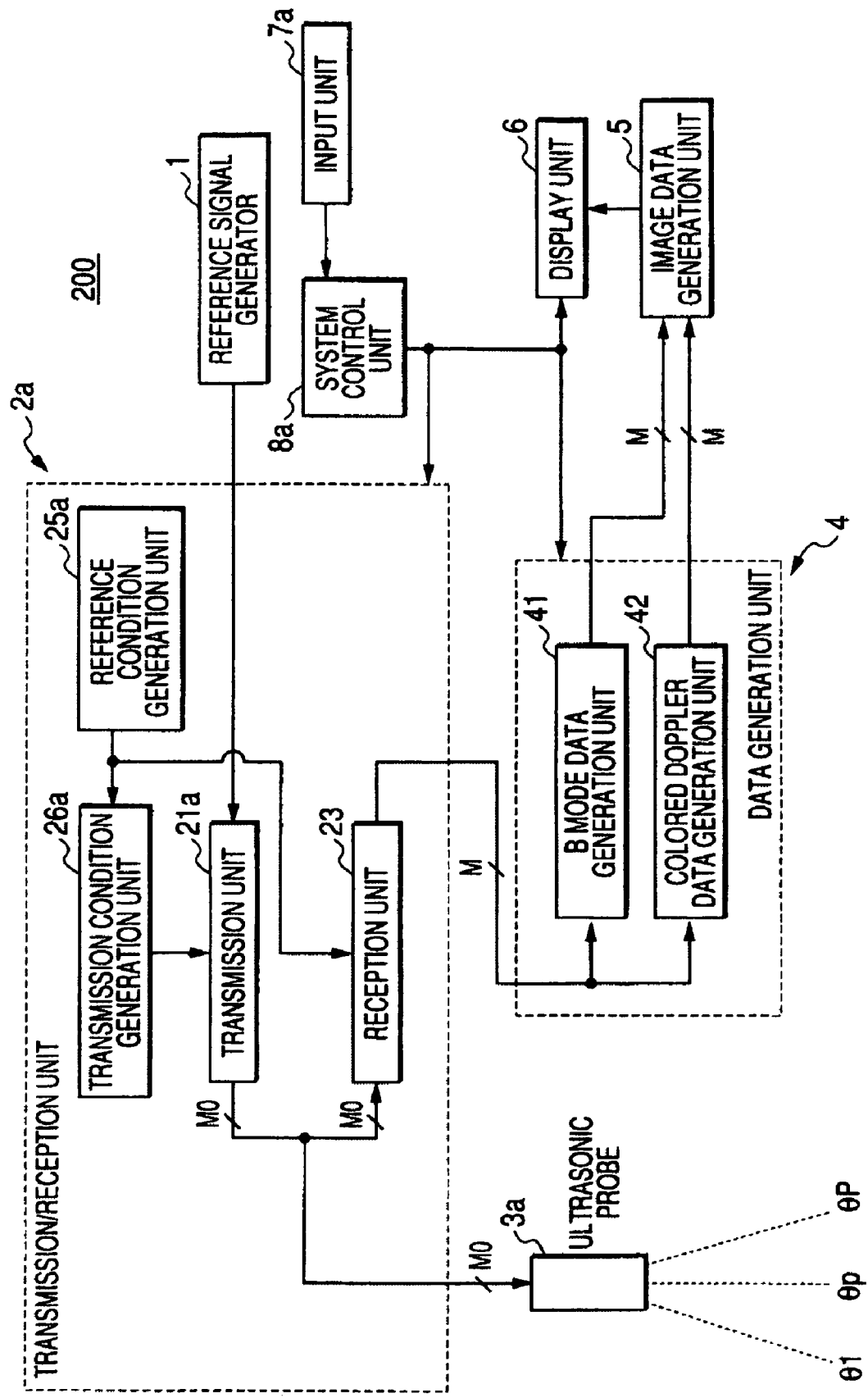
FIG. 10 is a block diagram showing an overall configuration of an ultrasonic diagnostic apparatus according to a second embodiment of the present invention.
Figure 11:
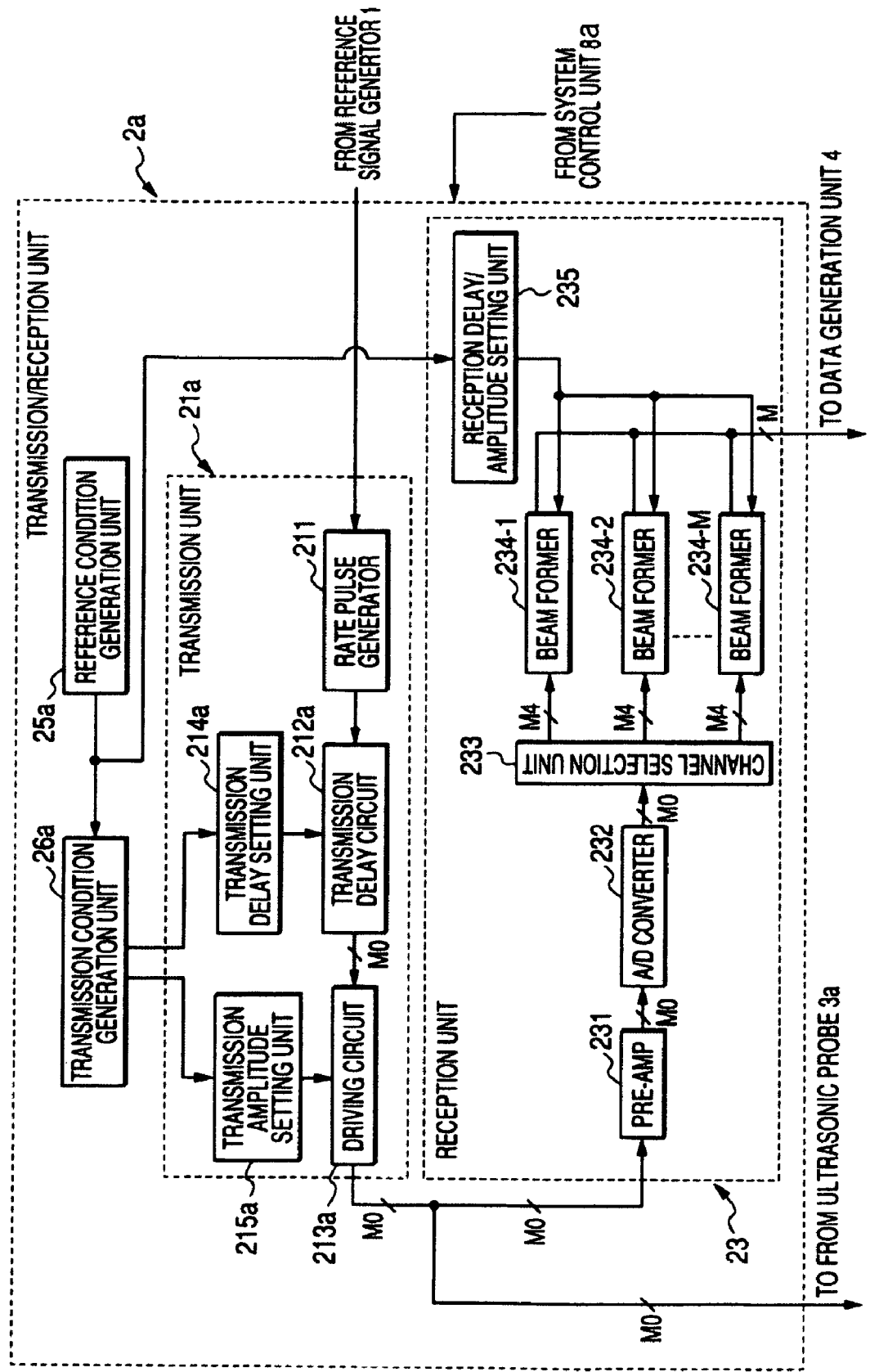
FIG. 11 is a block diagram showing a configuration of a transmission/reception unit in the second embodiment shown in FIG. 10.

FIG. 10 is a block diagram showing the overall configuration of the ultrasonic diagnostic apparatus according to the second embodiment and FIG. 11 is a block diagram showing the configuration of the transmission/reception unit constituting the ultrasonic diagnostic apparatus. In the ultrasonic diagnostic apparatus according to the second embodiment shown in FIG. 10, units having the same configurations and functions as the units of the ultrasonic diagnostic apparatus according to the first embodiment are denoted by the same reference numerals and detailed description will be omitted.

The ultrasonic diagnostic apparatus 200 according to the second embodiment shown in FIG. 10 includes a sector-scanning ultrasonic probe 3a in which M0 transducer elements are arranged linearly and which performs ultrasonic transmission and reception with respect to the object and a transmission/reception unit 2a for supplying driving pulses to the transducer elements and phase-matching adding reception signals obtained from the transducer elements. The ultrasonic diagnostic apparatus 200 further includes a data generation unit 4, an image data generation unit 5, a display unit 6, a reference signal generator 1, all of which have the same configurations and functions as those of the ultrasonic diagnostic apparatus 100 according to the first embodiment, and an input unit 7a for initializing patient information or the apparatus, and a system control unit 8a comprehensively controlling the above-mentioned units of the ultrasonic diagnostic apparatus 200.

The transmission/reception unit 2a shown in FIG. 11 includes a transmission unit 21a for supplying the driving pulses to a plurality of (M0) transducer elements of the sector-scanning ultrasonic probe 3a, a reception unit 23 for phase-matching adding the reception signals obtained from the transducer elements, a reference condition generation unit 25a for generating a reference delay condition and a reference amplitude condition for transmission in the non-simultaneous and parallel reception as the reference conditions, and a transmission condition generation unit 26a for generating a transmission delay condition and a transmission amplitude condition for the simultaneous and parallel reception as the transmission conditions on the basis of the reference delay condition and the reference amplitude condition generated by the reference condition generation unit 25a.

The transmission unit 21a includes a rate pulse generator 211, a transmission delay circuit 212a, a driving circuit 213a, a transmission delay setting unit 214a, and a transmission amplitude setting unit 215a.

The rate pulse generator 211 generates rate pulses for determining a repetition period of transmission ultrasound by dividing the frequency of continuous waves supplied from the reference signal generator 1. The transmission delay circuit 212a having M0 channels gives a predetermined delay time to the rate pulses on the basis of a delay control signal supplied from the transmission delay setting unit 214a. The driving circuit 213a having M0 channels generates driving pulses having a predetermined amplitude in synchronization with the rate pulses to which the predetermined delay time is given by the transmission delay circuit 212a on the basis of an amplitude control signal supplied from the transmission amplitude setting unit 215a.

On the other hand, the transmission delay setting unit 214a sets the delay time of the transmission delay circuit 212a on the basis of the transmission delay condition generated from the transmission condition generation unit 26a. Similarly, the transmission amplitude setting unit 215a sets the driving amplitude of the driving circuit 213a on the basis of the transmission amplitude condition generated from the transmission condition generation unit 26a.

The reference condition generation unit 25a of the transmission/reception unit 2a generates the reference delay condition τpo(m) and the reference amplitude condition Ao(m) in the transmission direction θp at the time of the non-simultaneous and parallel reception when image data are generated using an acoustic transmission field formed by converging ultrasound at a predetermined distance in transmission directions θ1 to θp and an acoustic reception field formed with the same central axis as the central axis of the acoustic transmission field.

A method of generating the transmission delay condition and the transmission amplitude condition in the transmission condition generation unit 26a will be described with reference to FIG. 12. The transmission delay condition τp(m) and the transmission amplitude condition Ap(m) generated by the transmission condition generation unit 26a when ultrasound are transmitted in the transmission direction θp of the sector scanning are described below.

Figure 12:
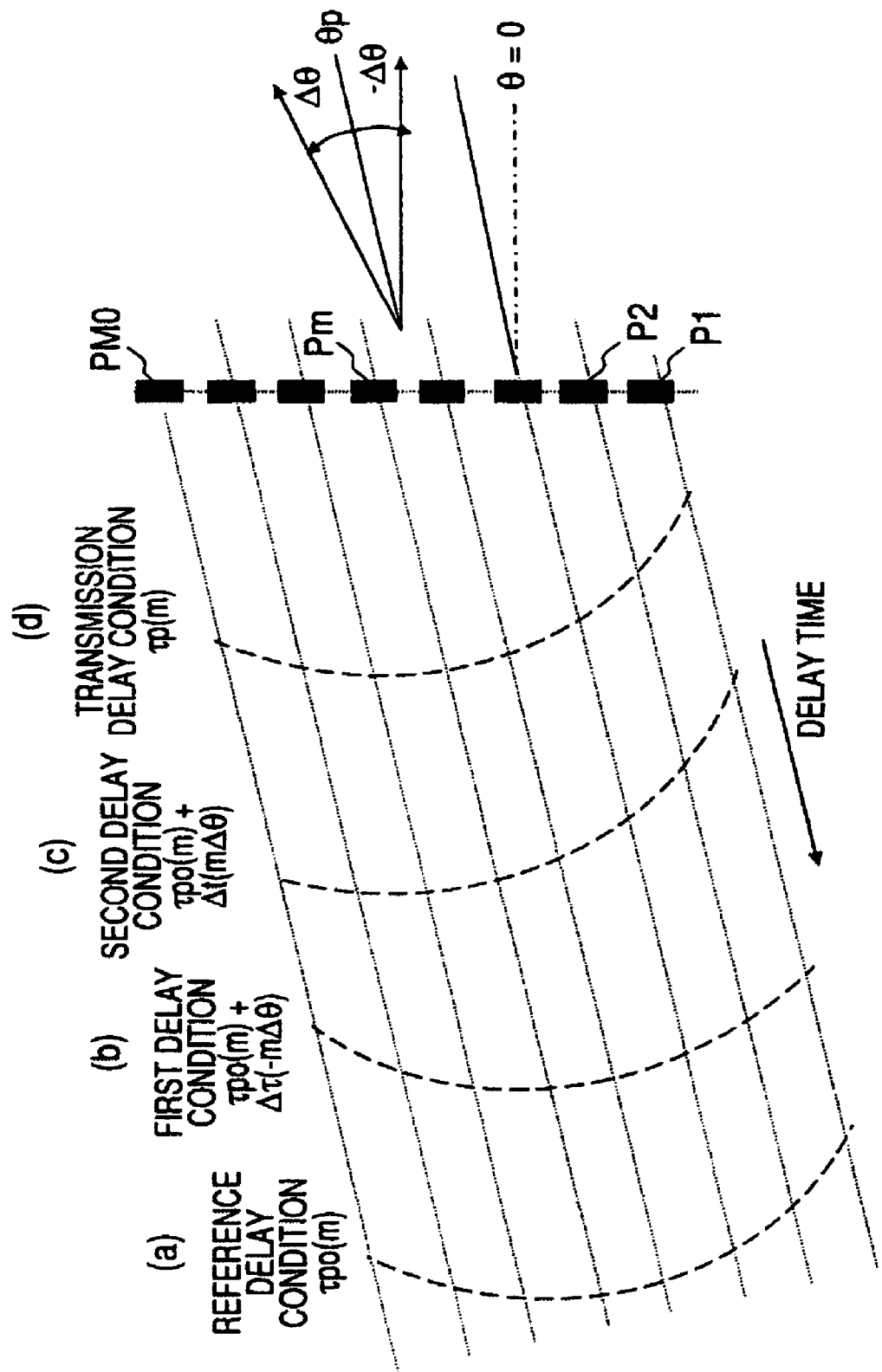
FIG. 12 is a schematic diagram showing a function of a transmission condition generation unit in the second embodiment shown in FIG. 10.

As shown in FIG. 12, the transmission condition generation unit 26a generates a first driving pulse Hpo(m,Δθ) for transmitting the ultrasound in the transmission direction θp-Δθ and a second driving pulse Hpo(m,Δθ) for transmitting the ultrasound in the transmission direction θp+Δθ on the basis of a reference driving pulse Hpo(m,0) having the reference delay condition τpo(m) (FIG. 12A) and the reference amplitude condition Ao(m) for transmitting the ultrasound in the transmission direction θp, and obtains a driving pulse Hp(m) for the simultaneous and parallel reception by combining the first and second driving pulses.

In this case, the first driving pulse Hpo(m,-Δθ) has the reference amplitude condition Ao(m) and a first delay condition τpo(m)+Δτ(-mΔθ) (FIG. 12B) and the second driving pulse Hpo(m,Δθ) has the reference amplitude condition Ao(m) and a second delay condition τpo(m)+Δτ(mΔθ) (FIG. 12C). Here, Δτ(-mΔθ) and Δτ(MΔθ) correspond to the delay conditions for deflecting the transmission ultrasound in the directions -Δθ and Δθ.

An acoustic transmission field having uniform transmission intensity and proper beam width in the direction θp is formed by driving the M0 transducer elements P1 to PM0 by the driving pulses Hp(m) with the transmission delay time τp(m) (FIG. 12D) obtained by combining the first driving pulse Hpo(m,-Δθ) and the second driving pulse Hpo(m,Δθ).

It will be described below that the transmission delay condition τp(m) and the transmission amplitude condition Ap(m) for forming an acoustic transmission field having uniform intensity and beam width suitable for the simultaneous and parallel reception are generated on the basis of the reference delay condition τpo(m) and the reference amplitude condition Ao(m) for setting transmission directivity in the transmission direction θp.

In this case, when it is assumed that the reference driving pulse for a transducer element Pm based on the reference delay condition τpo(m) and the reference amplitude condition Ao(m) is Hpo(m,0), the driving pulse Hp(m) of which the transmission conditions are generated by the transmission condition generation unit 26 can be expressed by Expression 7.

$$Hp(m) = \qquad (7)$$
$$Ap(m)Wp\{t - \tau p(m)\}\exp\{j\omega(t - \tau p(m)\} = Hpo(-m\Delta\theta) + Hpo(m\Delta\theta) =$$
$$Ao(m)Wo\{t - (\tau po(m) + \Delta\tau(-m\Delta\theta))\}$$
$$\exp[j\omega\{t - (\tau po(m) + \Delta\tau(-m\Delta\theta))\}] +$$
$$ao(m)Wo\{t - (\tau po(m) + \Delta\tau(m\Delta\theta))\}$$
$$\exp[j\omega\{t - (\tau po(m) + \Delta\tau(m\Delta\theta))\}]$$

Here, Wp(t) and Wo(t) denote envelope functions for the driving pulse Hp(m) and the reference driving pulse Hpo(m), Hpo(m,-Δθ) and Hpo(m,Δθ) denote the first driving pulse and the second driving pulse for allowing the transmission of the ultrasound in the transmission directions θp-Δθ and θp+Δθ. The delay conditions of the driving pulses are generated by adding the delay conditions -Δτ(mΔθ) and Δτ(mΔθ) to the reference delay condition τp(m). Here, when the envelope functions are much longer than the period of the driving pulses (that is, a reciprocal of a central frequency of the ultrasound), Expression 8 is established approximately.

$$Wo\{t-(\tau po(m)+\Delta\tau(-m\Delta\theta))\} \approx Wo\{t-(\tau po(m)+\Delta\tau(m\Delta\theta))\} \approx Wo\{t-\tau po(m)\} \qquad (8)$$

Accordingly, the transmission delay condition τp(m) and the transmission amplitude condition Ap(m) of the driving pulse Hp(m) can be expressed by Expression 9 using the reference delay condition τpo(m) and the reference amplitude condition Ao(m) of the reference driving pulse Hpo(m,0).

$$Hp(m) = Ao(m)Wo\{t - \tau po\}\Big[\exp\{j\omega(t - (\tau po(m) + \Delta\tau(-m\Delta\theta)))\} + \qquad (9)$$
$$\exp\{j\omega(t - (\tau po(m) + \Delta\tau(m\Delta\theta)))\} =$$
$$Ap(m)Wp\{t - \tau p(m)\}\exp[j\omega\{t - \tau p(m)\}]$$
$$Ap(m) = 2Ao(n)[\cos\{(\omega(\tau po(m) + \Delta\tau(-m\Delta\theta)) -$$
$$\omega(\tau po(m) + \Delta\tau(m\Delta\theta)))/2\}]$$
$$Wp\{t - \tau p(m)\} \approx Wo(t - \tau po(m)\}$$
$$\tau p(m) = \tau po(m) + \frac{\Delta\tau(-m\Delta\theta)) + \Delta\tau(m\Delta\theta)}{2}$$

Figure 7:
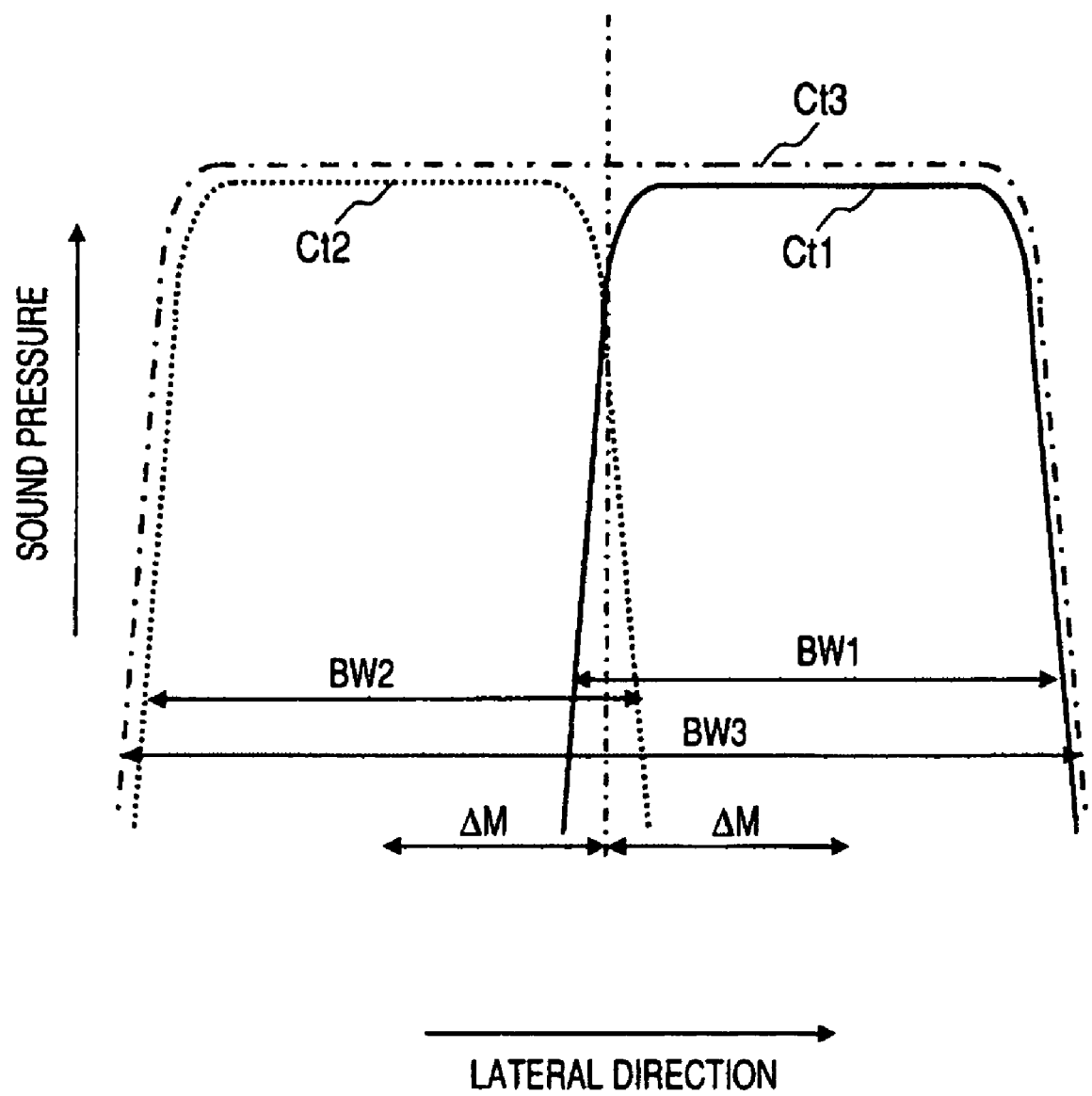
FIG. 7 is a diagram showing the acoustic transmission field in the first embodiment shown in FIG. 1.
Figure 8:
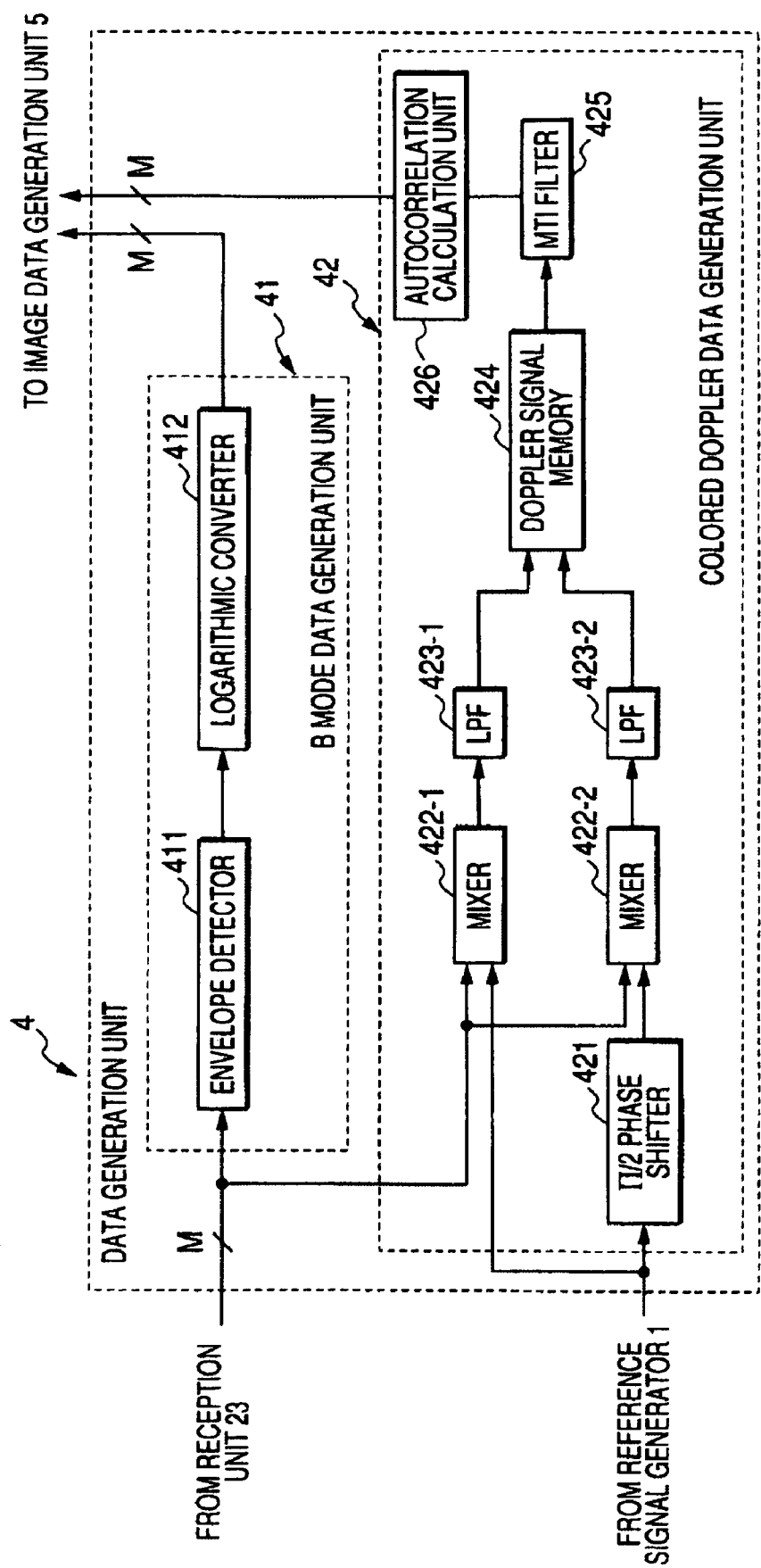
FIG. 8 is a block diagram showing a configuration of a data generation unit in the first embodiment shown in FIG. 1.

As described above, an acoustic transmission field substantially equivalent to the acoustic transmission field shown in FIG. 7 can be obtained by driving the transducer elements P1 to PM0 by the driving pulse Hp(m) based on the transmission delay condition τp(m) and the transmission amplitude condition Ap(m) generated by Expression 9. However, in the second embodiment, the lateral direction X in FIG. 7 is substituted with the angle θ and ΔM is substituted with Δθ.

That is, the transmission condition generation unit 26a generates the transmission delay condition τp(m) and the transmission amplitude condition Ap(m) through the above-mentioned calculations using the reference delay condition τpo(m) and the reference amplitude condition Ao(m) for transmission supplied from the reference condition generation unit 25a, and supplies the result to the transmission delay setting unit 214a and the transmission amplitude setting unit 215a of the transmission unit 21a. The transmission delay setting unit 214a and the transmission amplitude setting unit 215a set the delay time of the transmission delay circuit 212a and the driving amplitude of the driving circuit 213a on the basis of the transmission delay condition τp(m) and the transmission amplitude condition Ap(m).

The B mode data generation unit 41 of the data generation unit 4 shown in FIG. 10 generates B mode data by processing the M-channel reception signals output from the beam former 234-1 to 234-M of the reception unit 23. The colored Doppler data generation unit 42 generates colored Doppler data by processing the reception signals. The image data generation unit 5 sequentially stores the B mode data and the colored Doppler data generated by the data generation unit 4 and generates two-dimensional B mode image data and two-dimensional colored Doppler image data.

The display unit 6 performs a scanning conversion process corresponding to a predetermined display format to the B mode image data or the colored Doppler image data generated in the image data generation unit 5, performs a D/A conversion and a television format conversion, and displays the converted data on the monitor.

On the other hand, the input unit 7a includes input devices such as a display panel or a keyboard, a track ball, a mouse, selection buttons, and input buttons on an operation panel, and is used to input of patient information, set data collection conditions and display condition, input command signals, etc. Specifically, in the second embodiment, the input unit 7a performs the setting of the number of channels M4 for phase-matching addition, the number M for simultaneous and parallel reception, and the deflection angles $-\Delta\theta$ and $\Delta\theta$ of the transmission ultrasound, and the selection of the reference amplitude condition and the simultaneous and parallel reception mode/non-simultaneous and parallel reception mode.

The system control unit 8a systematically controls the transmission/reception unit 2a, the data generation unit 4, the image data generation unit 5, and the overall system. The system control unit 8a performs the control for performing the simultaneous and parallel reception in the M directions of the acoustic transmission field and the control for performing the sector scanning to the object by supplying control signals to the reception unit 23 of the transmission/reception unit 2a.

A procedure of generating image data in a simultaneous and parallel reception mode according to the second embodiment will be described with reference to FIG. 13. Here, for the purpose of easy description, it is assumed that the number of transducer elements of the transmission transducer element group and the number of transducer elements of the reception transducer element group are M0, but the invention is not limited to the assumption. In addition, a procedure of generating the B mode image data is described below, but the image data such as the colored Doppler image data can be generated through the same procedure as the first embodiment.

The operator of the ultrasonic diagnostic apparatus 200 sets a probe ID of the ultrasonic probe 3a and the conditions necessary for collecting image data through the input unit 7a shown in FIG. 10, and stores these information in a storage circuit in the system control unit 8a. The initial setting conditions includes the number of channels M4 for phase-matching addition, the number of directions M for simultaneous and parallel reception, and the deflection angles $-\Delta\theta$ and $\Delta\theta$ of the transmission ultrasound, and a reference amplitude condition (S11 in FIG. 13).

When the initial setting is finished, the operator selects the simultaneous and parallel reception mode and then starts the transmission and reception of ultrasound by fixing the end (ultrasonic transmission and reception surface) of the ultrasonic probe 3a to a predetermined position on the surface of the object. At this time, the system control unit 8a supplies the information on the deflection angles $-\Delta\theta$ and $\Delta\theta$ of the transmission ultrasound and the information on the reference amplitude condition stored in its own storage circuit to the transmission condition generation unit 26a, and stores the information described above in the storage circuits of the respective units.

Figure 13:
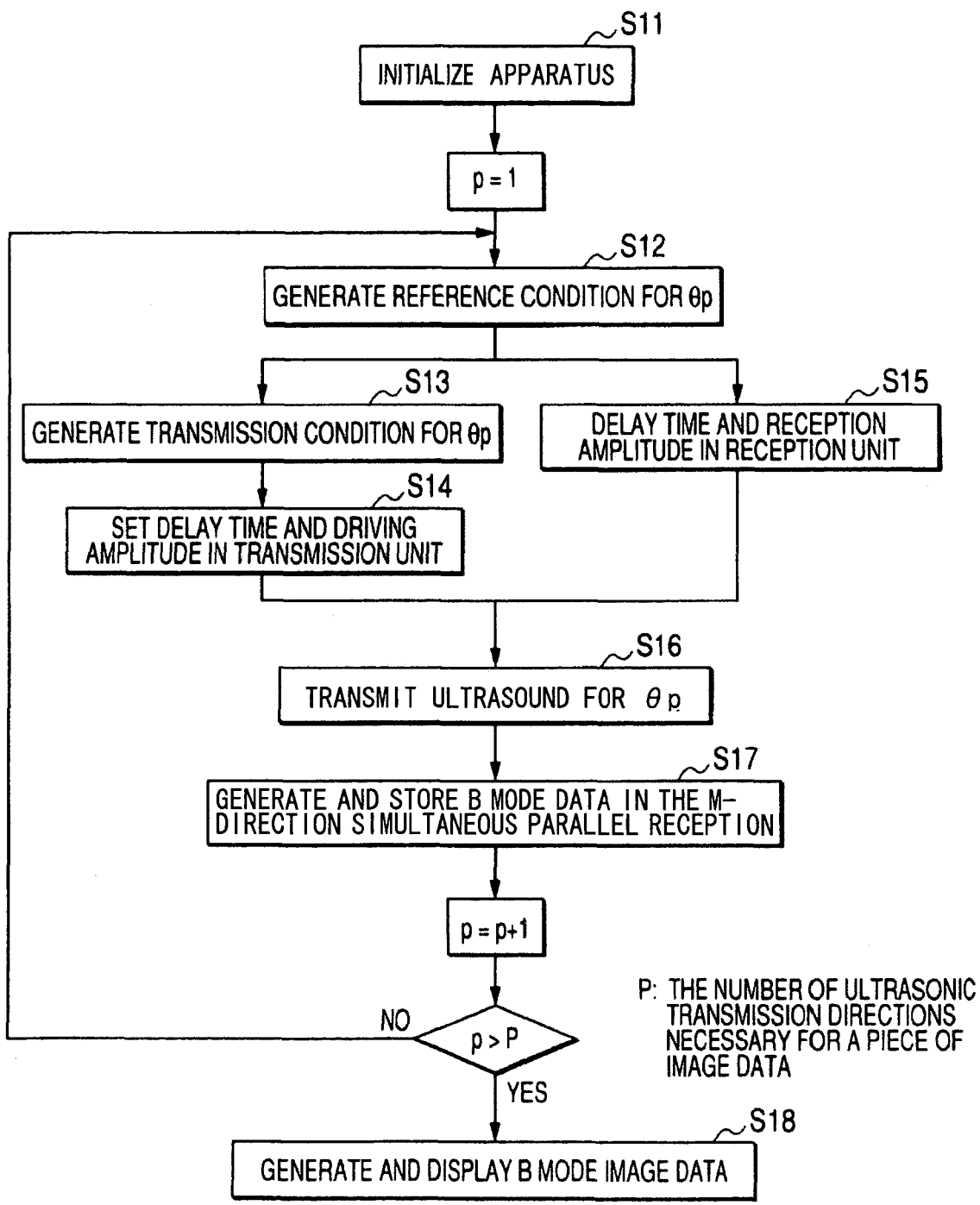
FIG. 13 is a flowchart illustrating a procedure in which image data are generated in the second embodiment shown in FIG. 10.

The reference condition generation unit 25a of the transmission/reception unit 2a generates the reference delay condition $\tau1o(m)$ and the reference amplitude condition $Ao(m)$ for transmission on the basis of the information on the number of transducer elements M0 of the transmission transducer element group and the reception transducer element group, the information on the selection of the reference amplitude condition and the information on the initial transmission direction $\theta1$ (p=1) supplied from the system control unit 8a, and then supplies these condition to the transmission condition generation unit 26a (S12 in FIG. 13).

The transmission condition generation unit 26a generates the transmission delay condition $\tau1(m)$ and the transmission amplitude condition $A1(m)$ by substituting the reference delay condition $\tau1o(m)$ and the reference amplitude condition $Ao(m)$ supplied from the reference condition generation unit 25a and the deflection angles $-\Delta\theta$ and $\Delta\theta$ of the transmission ultrasound stored in its own storage circuit for, for example, Expression 9 (S13 in FIG. 13).

Next, the transmission condition generation unit 26a supplies the transmission delay condition $\tau1(m)$ to the transmission delay setting unit 214a and supplies the transmission amplitude condition $A1(m)$ to the transmission amplitude setting unit 215a. The transmission delay setting unit 214a and the transmission amplitude setting unit 215a set the delay time of the transmission delay circuit 212a and the driving amplitude of the driving circuit 213a on the basis of the condition information (S14 in FIG. 13).

On the other hand, the reception delay/amplitude setting unit 235 of the reception unit 23 set the delay time and the amplitude of the beam formers 234-1 to 234-M for reception on the basis of the reference delay condition and the reference amplitude condition for reception supplied from the reference condition generation unit 25a (S15 in FIG. 13).

In the ultrasonic transmission in the first transmission direction $\theta1$, the rate pulse generator 211 shown in FIG. 11 generates a rate pulse for determining the repetition period of a driving pulse by dividing the frequency of a reference signal supplied from the reference signal generator 1 and supplies the rate pulse to the transmission delay circuit 212a. The transmission delay circuit 212a with M0 channels gives delay time set by the transmission delay setting unit 214a to the rate pulse and supplies the rate pulses to the driving circuit 213a.

The driving circuit 213a generates a driving pulse which has driving amplitude set by the transmission amplitude setting unit 215a and has the delay time synchronized with the rate pulse supplied from the transmission delay circuit 212a, supplies the driving pulse to transducer elements P1 to PM0 of the ultrasonic probe 3a, and transmits the ultrasound to the object (S16 in FIG. 13).

The ultrasound transmission to the object by driving the transducer elements P1 to PM0 is partially reflected at the boundary surfaces between organs or tissues having different acoustic impedance. Furthermore, the frequency of ultrasound is Doppler-shifted when the ultrasound is reflected at the moving reflectors such as cardiac wall or blood cells.

The reflected ultrasound (reception ultrasounds) from tissues or blood cells in the object is received by the transducer elements P1 to PM0 and is converted into electrical signals (reception signals). The reception signals are supplied to the reception unit 23, amplified into a predetermined magnitude by the pre-amplifier 231, and converted into digital signals by the A/D converter 232.

The M0 channel reception signals converted into the digital signals are supplied to the channel selection unit 233. The channel selection unit 233 selects M reception signal groups with M4 adjacent channels among the M0 channel reception signals (M4<M0), and supplies the M reception signal groups to the M-channel beam formers 234-1 to 234-M. The respective beam formers 234-1 to 234-M perform the dynamic focusing by phase-matching addition of the M4-channel reception signals.

The M-channel reception signals obtained by the phase-matching addition in the beam formers 234-1 to 234-M are supplied to the B mode data generation unit 41 of the data generation unit 4 shown in FIG. 10, subjected to the envelope detection and the logarithmic conversion and stored in the B mode data storage area of the image data generation unit 5 as the B mode data in the transmission direction θ1 (S17 in FIG. 13).

Next, the system control unit 8a controls the reference condition generation unit 25a and the transmission condition generation unit 26a of the transmission/reception unit 2a. The reference condition generation unit 25a generates the reference delay condition τ2o(m) and the reference amplitude condition Ao(m) for transmitting the ultrasound in the transmission direction θ2 (p=2) adjacent to the direction θ1 (S12 in FIG. 13). The transmission condition generation unit 26a generates the transmission delay condition τ2(m) and the transmission amplitude condition A2(m) in the transmission direction θ2 on the basis of the reference conditions (S13 in FIG. 13).

The transmission delay setting unit 214a and the transmission amplitude setting unit 215a set the delay time of the transmission delay circuit 212a and the driving amplitude of the driving circuit 213a on the basis of the transmission conditions (S14 in FIG. 13). The driving circuit 213a generates the driving pulse with the driving amplitude synchronized with the rate pulses to which the predetermined delay time is given by the transmission delay circuit 212a and transmits the ultrasound in the direction θ2 of the object by driving the transducer elements P1 to PM0 (S16 in FIG. 13).

Subsequently, the reception unit 23 simultaneously receives in parallel the reception ultrasounds corresponding to the transmission ultrasound. The data generation unit 4 generates the B mode data with respect to the transmission direction θ2 by processing the reception signals, and stores the B mode data in the B mode data storage area of the image data generation unit 5 (S17 in FIG. 13).

The transmission and reception of the ultrasound are performed in the transmission directions θp (where p is in the range of 3 to P) through the same procedure, the obtained B mode data are stored in the B mode data storage area of the image data generation unit 5, and thus two-dimensional or three-dimensional B mode image data are generated. The B mode image data are performed a predetermined scanning conversion and displayed on the monitor of the display unit 6 (S18 in FIG. 13).

According to the second embodiment described above, when the simultaneous and parallel reception is performed to a diagnostic area of an object by using the sector-scanning ultrasonic probe, the beam distortion in the acoustic transmission/reception field in the simultaneous and parallel reception or the non-uniformity of transmission/reception sensitivity in the respective directions of the parallel reception can be reduced with a simple circuit configuration.

In the second embodiment, it is possible to obtain the acoustic transmission field having excellent uniformity and a rapid attenuation characteristic at the sides thereof by using the reference amplitude condition based on the Sinc function.

Accordingly, since the transmission ultrasounds is only irradiated to the area where the simultaneous and parallel reception is performed, it is possible to use the transmission energy effectively, to reduce the side lobe or the artifact due to multiple reflection, and to generate image data excellent in sensitivity.

That is, according to the second embodiment, since a uniform acoustic transmission field can be formed in wide area, it is possible to increase the number of directions for the simultaneous and parallel reception and thus to generate image data excellent in temporal resolution, spatial resolution, and detection capability. Since the transmission unit forming the acoustic transmission field can be embodied with a simple circuit configuration, it is possible to provide the ultrasonic diagnostic apparatus and the ultrasound transmitting method excellent in cost performance.

An embodiment of the present invention has been described so far, the present invention is not limited thereto. Rather, they may be modified in implementing them. In the embodiments, for example, it has been described that the acoustic transmission field substantially equivalent to the acoustic transmission field obtained by combining two driving pulse groups is formed by controlling the delay time and the driving amplitude of the single driving pulse group. However, the transmission condition generation unit 26 or the transmission condition generation unit 26a may generate a transmission delay condition and a transmission amplitude condition for obtaining an acoustic transmission field substantially equivalent to an acoustic transmission field obtained by combining 3 or more driving pulse groups.

For example, a delay time τa(m) and a driving amplitude Aa(m) for obtaining the acoustic transmission field equivalent to the acoustic transmission field obtained by combining 4 driving pulse groups PL1 to PL4 with a combination interval 2ΔM can be obtained by Expression 10.

On the other hand, although the transmission signal group has an amplitude distribution based on the Sinc function in the embodiments described above, but may have other amplitude distributions. For example, since it is possible to reduce the influence of the discontinuity at the sides of the amplitude distribution by multiplying the Sinc function by a Hamming window function, it is possible to form a more excellent acoustic transmission field.

$$Ha(m) = Ao(m)Wo\{t - \tau o(m)\}[\exp\{j\omega(t - \tau o(-\Delta 3M))\} + \quad (10)$$

$$\exp\{j\omega(t - \tau o(m - \Delta M))\} + \exp\{j\omega(t - \tau o(m + \Delta M))\} +$$

$$\exp\{j\omega(t - \tau o(m + 3\Delta M))\}] =$$

$$Aa(m)Wa\{t - \tau a(m)\}\exp[j\omega\{t - \tau a(m)\}]$$

$$Aa(m) = Ao(m)G$$

$$Wa\{t - \tau a(m)\} \approx Wo\{t - \tau a(m)\}$$

$$\tau a(m) = \frac{1}{4}(\tau o(m - 3\Delta M) + \tau o(m - \Delta M) +$$

$$\tau o(m + \Delta M) + \tau o(m + 3\Delta M)) - \frac{\Theta}{\omega}$$

$$G = \mathrm{abs}\left[\alpha \cdot \cos\left[\omega\left\{\frac{\tau a(m) - \tau b(m)}{2}\right\}\right] - j\beta \cdot \sin\left[\omega\left\{\frac{\tau a(m) - \tau b(m)}{2}\right\}\right]\right]$$

$$\Theta = \mathrm{arg}\left[\alpha \cdot \cos\left[\omega\left\{\frac{\tau a(m) - \tau b(m)}{2}\right\}\right] - j\beta \cdot \sin\left[\omega\left\{\frac{\tau a(m) - \tau b(m)}{2}\right\}\right]\right]$$

$$\alpha = \frac{1}{2}\left(\cos\left[\omega\left\{\frac{\tau o(m - 3\Delta M) - \tau o(m - \Delta M)}{2}\right\}\right] +$$

-continued $$\beta = \frac{1}{2}\left(\cos\left[\omega\left\{\frac{\tau o(m+\Delta M) - \tau o(m+\Delta 3M)}{2}\right\}\right]\right) -$$
$$\cos\left[\omega\left\{\frac{\tau o(m-3\Delta M) - \tau o(m-\Delta M)}{2}\right\}\right] -$$
$$\cos\left[\omega\left\{\frac{\tau o(m+\Delta M) - \tau o(m+\Delta 3M)}{2}\right\}\right]\right)$$

$$\tau a(n) = \frac{\tau o(m - 3\Delta M) + \tau o(m - \Delta M)}{2}$$

$$\tau a(n) = \frac{\tau o(m + \Delta M) + \tau o(m + \Delta 3M)}{2}$$

In the above-mentioned embodiments, the ultrasonic probe 3 and the ultrasonic probe 3a in which the transducer elements are arranged in one dimension have been described, but an ultrasonic probe in which the transducer elements are arranged in two dimensions may be employed. The ultrasonic scanning method is not limited to the convex scanning method and the sector scanning method, but may employ other scanning methods such as a linear scanning method and a radial scanning method.

In the above-mentioned embodiments, there has been described an example that the reference condition generation unit 25 or the reference condition generation unit 25a generates the reference delay condition and the reference amplitude condition and the transmission condition generation unit 26 or the transmission condition generation unit 26a generates the transmission delay condition and the transmission amplitude condition. However, the reference condition generation unit 25 or the reference condition generation unit 25a may generate at least one of the reference delay condition and the reference amplitude condition as the reference transmission condition, and the transmission condition generation unit 26 or the transmission condition generation unit 26a may generate at least one of the transmission delay condition and the transmission amplitude condition as the transmission condition.

Numerous modifications and variations of the present invention are possible in light of the above teachings. It is therefore to be understood that, within the scope of the appended claims, the present invention can be practiced in a manner other than as specifically described herein.

What is claimed is:

1. An ultrasonic diagnostic apparatus for forming an acoustic transmission field to an object to be examined, comprising:
   a plurality of transducer elements configured to transmit ultrasound to the object;
   a reference signal generation unit configured to output a continuous wave signal so as to generate the ultrasound;
   a reference condition generation unit configured to generate reference conditions including delay time and driving amplitude to drive the plurality of transducer elements;
   a transmission condition generation unit configured to generate a transmission delay time condition and a transmission driving amplitude condition to form an acoustic transmission field for simultaneous and parallel reception based on the reference conditions;
   a delay time setting unit configured to set delay time of driving signals based on the continuous wave signal provided from the reference signal generation unit, the driving signals being provided to the plurality of transducer elements;
   a driving amplitude setting unit configured to set driving amplitude of the driving signals based on the continuous wave signal provided from the reference signal generation unit;
   an A/D converter configured to A/D convert signals obtained from the plurality of transducer elements based on reflected ultrasound received from a plurality of directions by the transmission of the ultrasound;
   a channel selection unit configured to select a plurality and different sets of channel signals from a plurality of channel signals outputted from the A/D converter;
   a plurality of beam formers configured to give the delay time and the driving amplitude provided from the reference condition generation unit respectively to the plurality of sets of channel signals selected by the channel selection unit, each of the beam formers adding the delay time and the driving amplitude given the channel signals; and
   an image data generation unit configured to generate image data to display an image,
   wherein the transmission condition generation unit is configured to output the transmission delay time condition and the transmission driving amplitude condition to the delay time setting unit and the driving amplitude setting unit, which are obtained by the following expressions, respectively, $\tau(m)=\{\tau_o(m-\Delta M)+\tau_o(m+\Delta M)\}/2$, and $A(m)=2A_0(m)[\cos\{(\omega\tau_0(m-\Delta M)-\omega\tau_0(m+\Delta M))/2\}]$, where "m" is a number of one of the plurality of transducer elements, $\tau(m)$ is the transmission delay time condition, $\tau_0(m)$ is a reference delay time condition, $\Delta M$ is a shift of the transducer elements in an arrangement direction, $A(m)$ is the transmission driving amplitude condition, $A_0(m)$ is a reference driving amplitude condition, and $\omega$ is a central frequency of ultrasound.

2. The ultrasonic diagnostic apparatus according to claim 1, wherein the transmission condition generation unit is configured to generate the transmission condition by combining the reference conditions corresponding to a plurality of directions.

3. The ultrasonic diagnostic apparatus according to claim 1, wherein the transmission condition generation unit is configured to generate the transmission condition by combining the reference conditions corresponding to a plurality of directions having a predetermined angle to a transmission direction of ultrasound.

4. The ultrasonic diagnostic apparatus according to claim 1, wherein the reference condition generation unit is configured to generate at least one of a reference delay condition for setting the delay time of the driving signals and a reference amplitude condition for setting amplitude of the driving signals in non-simultaneous and parallel reception, the driving signals being provided to the plurality of transducer elements.

5. The ultrasonic diagnostic apparatus according to claim 4, wherein the reference condition generation unit is configured to generate the reference amplitude condition based on a Since function.

6. The ultrasonic diagnostic apparatus according to claim 1, wherein the reception unit is configured to set a plurality of reception directions corresponding to a beam width of the acoustic transmission field formed by driving the transducer elements.

7. The ultrasonic diagnostic apparatus according to claim 1, further comprising:

an element selection unit configured to select a plurality of adjacent transducer elements from the plurality of transducer elements which are provided with the driving signal, wherein signals obtained from the selected plurality of adjacent transducer elements are provided to the A/D converter.

8. The ultrasonic diagnostic apparatus according to claim 1, further comprising:

an input unit configured to set the shift of the transducer elements ΔM and to set the reference driving amplitude condition $A_0(m)$.

* * * * *